United States Patent [19]

Hurwitz et al.

US005741492A

[11] Patent Number: 5,741,492

[45] Date of Patent: Apr. 21, 1998

[54] PREPARATION AND USE OF VIRAL VECTORS FOR MIXED ENVELOPE PROTEIN VACCINES AGAINST HUMAN IMMUNODEFICIENCY VIRUSES

[75] Inventors: Julia L. Hurwitz, Germantown; Randall J. Owens, Millington, both of Tenn.

[73] Assignee: St. Jude Children's Research Hospital, Memphis, Tenn.

[21] Appl. No.: 590,288

[22] Filed: Jan. 23, 1996

[51] Int. Cl.[6] .......................... A61K 45/00; A61K 39/42; A61K 38/00; C12N 15/00

[52] U.S. Cl. .................................... 424/208.1; 424/160.1; 424/199.1; 435/320.1; 514/44; 536/23.2

[58] Field of Search ............................. 424/160.1, 199.1, 424/208.1; 435/320.1; 514/44; 536/23.2

[56] References Cited

U.S. PATENT DOCUMENTS

| | | | |
|---|---|---|---|
| 5,081,226 | 1/1992 | Berzofsky et al. | 530/324 |
| 5,169,763 | 12/1992 | Kieny et al. | 435/69.3 |

FOREIGN PATENT DOCUMENTS

| | | |
|---|---|---|
| 2181435 | 4/1987 | United Kingdom . |
| WO 87/06262 | 10/1987 | WIPO . |
| WO 90/12880 | 11/1990 | WIPO . |
| WO 92/22641 | 12/1992 | WIPO . |

OTHER PUBLICATIONS

Belshe, R. B. et al., "HIV Infection in Vaccinated Volunteers," *J. Amer. Medical Assoc. 272(6)*:431 (1994).

Burns, D. P. W. and R. C. Desrosiers, "Envelope Sequence Variation, Neutralizing Antibodies, and Primate Lentivirus Persistence," *Curr. Top. Microbiol. Immunol. 188*:185–219 (1994).

Chakrabarti, S. et al., "Vaccinia Virus Expression Vector: Coexpression of β–Galactosidase Provides Visual Screening of Recombinant Virus Plaques," *Mol. Cell. Biol. 5(12)*:3403–3409 (1985).

Cohen, J., "The HIV Vaccine Paradox," *Science 264*:1072–1074 (1994).

Cooney, E. L. et al., "Enhanced immunity of human immunodeficiency virus (HIV) envelope elicited by a combined vaccine regimen consisting of priming with a vaccinia recombinant expressing HIV envelope and boosting with gp160 protein," *Proc. Natl. Acad. Sci. USA 90*:1882–1886 (1993).

D'Hondt, E., "Possible approaches to develop vaccines against hepatitis A," *Vaccine 10(Suppl. 1)*:S48–S52 (1992).

Enami, M. and P. Palese, "High–Efficiency Formation of Influenza Virus Transfectants," *J. Virol. 65(5)*:2711–2713 (1991).

Enami, M. et al., "Introduction of site–specific mutations into the genome of influenza virus," *Proc. Natl. Acad. Sci. USA 87*:3802–3805 (1990).

Gorse, G. J., "Phase I/II Trials of Preventive HIV Vaccine Candidates. Dose and Schedule: Summary," *AIDS Res. Human Retroviruses 10(Suppl. 2)*:S141–S143 (1994).

Graham, B. S. et al., "Augmentation of Human Immunodeficiency Virus Type 1 Neutralizing Antibody by Priming with gp160 Recombinant Vaccinia and Boosting with rgp160 in Vaccinia–Naive Adults," *J. Inf. Dis. 167*:533–537 (1993).

(List continued on next page.)

*Primary Examiner*—Ponnathapura Achutamurthy
*Assistant Examiner*—Hankyel T. Park
*Attorney, Agent, or Firm*—Klauber & Jackson

[57] ABSTRACT

Polyenv vaccines are provided that comprise mixtures of at least 4–40 to about 10,000 different recombinant vaccinia viruses that each express a different HIV env variant or a portion thereof containing both constant and variable regions, as well as methods of making and using such polyenv vaccines and vaccinia viruses, including the use of the polyenv vaccine, in live, attenuated or inactivated form, for prophylaxis or treatment of HIV infection.

18 Claims, 4 Drawing Sheets

OTHER PUBLICATIONS

Graham, B. S. et al., "Vaccination of Vaccinia–Naive Adults with Human Immunodeficiency Virus Type 1 gp160 Recombinant Vaccinia Virus in a Blinded, Controlled, Randomized Clinical Trial," *J. Inf. Dis. 166*:244–252 (1992).

Grunwald-Beard, L. et al., "Killing of Burkitt–lymphoma–derived Daudi cells by ultraviolet–inactivated vaccinia virus," *J. Cancer Res. Clin. Oncol. 117*:561–567 (1991).

Hallenberger, S. et al., "Secretion of a Truncated Form of the Human Immunodeficiency Virus Type I Envelope Glycoprotein," *Virol. 193*:510–514 (1993).

Ito, T. et al., "Evolutionary Analysis of the Influenza A Virus M Gene with Comparison of the M1 and M2 Proteins," *J. Virol. 65(10)*:5491–5498 (1991).

Javaherian, K. et al., "Principal neutralizing domain of the human immunodeficiency virus type 1 envelope protein," *Proc. Natl. Acad. Sci. USA 86*:6768–6772 (1989).

Keefer, M. C. et al., "Safety Profile of HIV Vaccination: First 1000 Volunteers of AIDS Vaccine Evaluation Group," *AIDS Res. Human Retroviruses 10(Suppl. 2)*:S139–S140 (1994).

Kilpatrick, D. R. et al., "Effects of Deletion of the Cytoplasmic Domain upon Surface Expression and Membrane Stability of a Viral Envelope Glycoprotein," *J. Biol. Chem. 262(33)*:16116–16121 (1987).

McElrath, M. J. et al., "Immune Responses Elicited by Recombinant Vaccinia–Human Immunodeficiency Virus (HIV) Envelope and HIV Envelope Protein: Analysis of the Durability of Responses and Effect of Repeated Boosting," *J. Inf. Dis. 169*:41–47 (1994).

Richman, D. D., "Resistance, Drug Failure, and Disease Progression," *AIDS Res. Human Retroviruses 10(8)*:901–905 (1994).

Richman, D. D., "Resistance of Clinical Isolates of Human Immunodeficiency Virus to Antiretroviral Agents," *Antimicrob. Agents Chemother. 37(6)*:1207–1213 (1993).

Richman, D. D., "HIV Drug Resistance," *AIDS Res. Human Retroviruses 8(6)*:1065–1071 (1992).

Starcich, B. R. et al., "Identification and Characterization of Conserved and Variable Regions in the Envelope Gene of HTLV–III/LAV, the Retrovirus of AIDS," *Cell 45*:637–648 (1986).

Zagury, D. et al., "A group specific anamnestic immune reaction against HIV–1 induced by a candidate vaccine against AIDS," *Nature 332*:728–731 (1988).

Girard, M. et al., "Immunogenicity of Potential HIV Vaccines in Chimpanzees," *Int. Conf. AIDS 5*:541 Abstract Th.C.O.47 (1989).

Eichberg, J. W., "Experience with Seventeen HIV Vaccine Efficacy Trials in Chimpanzees," *Int. Conf. AIDS 7(2)*:88 Abstract F.A.2 (1991).

Gritz et al. (1990) J. Virol. 64:5948–57.

Perales et al. (1995) J. AIDS & Human Retrovirol. 10:27–35.

Rencher et al. (1995) AIDS Res. Human Retroviruses 11:1131–3.

Ruby et al. (1990) Immun. Cell Biol. 68:113–7.

Fahey et al., Status of immune–based therapies in HIV infection and AIDS Clin. Exp. Immunol. (Jan. 1992) 88, 1–5.

Fox, J.L., No winners against AIDS, Bio/Technology, (1994) vol. 12, Feb. p. 128.

Hird et al., Immunotherapy with Monoclonal Antibodies, Genes and Cancer, Edited by Carney et al., 183–189, see p. 185, paragraph 1, 1990.

Berman et al., Protection of chimpanzees from infection by HV–1 after vaccination with recombinant glycoprotein gp120 but not gp160, Nature, vol. 345, pp. 622–625, see Abstract, col. 3, line 62, col. 8, "Example 2", Jun. 1990.

Stephens et al., Antibodies are produced to the variable regions of the external envelope glycoprotein of HIV–1 in chimpanzees infected with the virus and baboons immunized with a candidate recombinant vaccine, J Gen Virol, 73, 1099–1106, see Abstract, p. 1992.

Dallo et al, Human Immune Response elicited by Highly Attenuated Variants of Vaccinia Virus and by an Attenuated Recombinant Expressing HIV–1 Envelope Protein, Virol 173, 323–329, see Abstract, Jul. 1989.

PREPARATION AND USE OF VIRAL VECTORS FOR MIXED ENVELOPE PROTEIN VACCINES AGAINST HUMAN IMMUNODEFICIENCY VIRUSES

STATEMENT AS TO RIGHT TO INVENTIONS MADE UNDER FEDERALLY-SPONSORED RESEARCH AND DEVELOPMENT

Part of the work performed during development of this invention utilized U.S. Government funds. This work was supported in part by NCI grants R01-CA57419-03 and Cancer Center Support Core Grant P30-CA21765.NIH-NIAID grants AI-32529 and P01-AI31596-04. The U.S. Government has certain rights in this invention.

BACKGROUND OF THE INVENTION

1. Technical Field of the Invention

The present invention relates to polyenv vaccines for human immunodeficiency virus (HIV), comprising a mixture of at least 4–40 and up to 10,000 recombinant vaccinia viruses that each express a different variant of an HIV envelope protein. The vaccines are suitable for the vaccination of mammals, including humans, in order to provide unexpectedly enhanced cellular and/or humoral immune responses to HIV infection. Additionally, the invention relates to methods for making and using such recombinant vaccinia viruses and polyenv vaccines.

2. Background Information

The AIDS virus is likely to claim tens of millions of lives by the year 2,000, constituting a worldwide health concern of top priority (see, DeVita, et al., *AIDS, Etiology, Diagnosis, Treatment and Prevention,* 3rd edition, J. B. Lippincott Co., Philadelphia, Pa. (1992); Wong-Staal, in *Virology*, pp 1529–1543; and Hirsch, et al., in *Virology*, pp. 1545–1570). The design of an effective HIV vaccine poses a particular challenge to immunologists, as the reverse transcriptase enzyme involved in the replication of HIV has a high error rate. This results in many mutant HIV strains having outer coat or envelope proteins with variant protein sequences. These variant envelope proteins are often recognized as different antigens by the mammalian immune system, which produces more than $10^9$ new lymphocytes per day for the sole purpose of countering foreign antigens. B and T-cells constitute, respectively, the humoral and cellular components of the immune response.

A good example of the qualitative strength of such immune responses is shown in HIV-infected patients and in SIV-infected macaques. In each case, successive rounds of infection, immunity, and establishment of variant HIVs or SIVs occur (Wrin, et al., *J. Acquir. Immune Defic. Syndr.* 7:211–219 (1994); Burns and Desrosiers, *Cur. Topics Microbiol. Immunol.* 188:185–219 (1994)). With each cycle, the diversity of HIV antigenic determinants (and the corresponding immune responses) are increased, such that these immune responses neutralize a broad range of SIV or HIV variants, and superinfection is largely inhibited.

However, AIDS patients develop compromised immune responses that become insufficient to prevent the HIV viral infection from overcoming the patient's immune system. This may be due in part to the establishment of HIV variants whose envelope variant proteins are not recognized by the patient's immune system and thus escape destruction (*Sci. Amer.* August 1995, pp). In such cases, even if the immune response is capable of preventing de novo infection (e.g., persistent mutation of the virus in privileged sequestered sites), the HIV infection may ultimately overcome the patient's immune response (Pantaleo et al., *Nature* 362:355–358 (1993); Embretson. et al., *Nature* 362:359–362 (1993)).

The identification of B- and T-cell antigenic determinants among HIV proteins remains incomplete. The HIV envelope protein has been characterized as having variable (V1–V5) and constant (C1–C5) regions. A peptide representative of the V3 region has been termed the principal neutralizing determinant (PND)(Javaherian. et al., *Proc. Natl. Acad Sci.* (USA) 86:6768–6772 (1989)), although other regions of the envelope protein may also be involved in eliciting an immune response. The full length envelope protein from HIV contains about 850 to 900 amino acids, with the variation in length due to hypermutation (Starcich et al., *Cell* 45:637 (1986)).

The first vaccines against HIV evaluated in clinical trials were designed to present single envelope proteins, or portions thereof, to the immune system. However, neutralizing responses towards a single or a few envelope proteins did not recognize diverse isolates of HIV and the individuals were not protected from infection (Belshe et al., *J. Am. Med Assoc.* 272:431–431 (1994); U.S. Pat. No. 5,169,763; PCT publication WO 87/06262; Zagury et al., *Nature* 332:728–731 (1988); Kieny et al., *Int. Conf. AIDS* 5:541 (1989); Eichberg, *Int. Conf. AIDS* 7:88 (1991); Cooney et al., *Proc. Natl. Acad Sci. USA* 90:1882–1886 (1993); Graham et al., *J. Infect. Dis.* 166:244–252 (1992); *J. Infect. Dis.* 167:533–537 (1993); Keefer et al., *AIDS Res. Hum. Retrovir.* 10 (Suppl. 2):S139–143 (1994); Gorse, *AIDS Res. Hum. Retrovir.* 10 (Suppl. 2): 141–143 (1994); McElrath et al., *J. Infect. Dis.* 169:41–47 (1994); Fauci, *Science* 264:1072–1073 (May 1994)).

Accordingly, there is a long-felt and pressing need to discover vaccines and methods that elicit an immune response that is sufficient to treat or prevent HIV infections.

SUMMARY OF THE INVENTION

The present invention is intended to overcome one or more deficiencies of the related arts.

To provide more effective HIV vaccines, the present invention provides polyenv vaccines comprising mixtures of at least 4–40, and up to 10,000 different recombinant vaccinia viruses, each expressing a different HIV envelope protein variant (EPV) (or a substantial portion thereof) that includes both constant and variable regions of the envelope protein. Preferably, each of the expressed envelope protein variants have a structure and/or immunogenicity similar to that of a native HIV envelope protein existing in an infected cell or HIV lipid bilayer, such as in an oligomeric form. Also provided are methods of making and using such recombinant vaccinia viruses and polyenv vaccines. In their use as a vaccine, each of the variant envelope proteins preferably induces a different subset of B and/or T cells, each subset responding to different envelope proteins and, hence, to multiple HIV variants. A mixture of this number, type and/or structure of envelope proteins is a now-discovered method for eliciting a strong, durable HIV-specific immune response with broad spectrum neutralizing activity.

The present inventors have discovered that polyenv vaccines of the present invention elicit unexpectedly enhanced immune responses by the expression and/or presentation of multiple envelope protein variants, each containing both constant and variable regions, preferably having a structure that is substantially similar to that of a native HIV envelope protein. The enhanced immune responses recognize HIV strains in addition to those strains expressing the envelope proteins provided in the polyenv vaccine. Thus, the aim of such a vaccine is to provide enhanced immune responses to a wide range of HIV strains, which immune responses are suitable for treating or preventing infection (or continued infection due to mutation) by different strains of the virus.

The present invention also provides env variant (EV) nucleic acid encoding (or complementary to) at least one antigenic determinant of an envelope protein variant (EPV). The EPV is preferably encoded by a recombinant vaccinia virus, as further provided in a polyenv vaccine of the present invention. The variant nucleic acid comprises at least one mutation that confers differing antigenic properties, or three dimensional structure, to the encoded EPV.

The present invention also provides a vaccine composition comprising a polyenv vaccine of the present invention, and a pharmaceutically acceptable carrier or diluent. The vaccine composition can further comprise an adjuvant and/or cytokine which enhances a polyenv vaccine immune response to at least one HIV strain in a mammal administered the vaccine composition. A polyenv vaccine of the present invention is capable of inducing an immune response inclusive of at least one of a humoral immune response (e.g., antibodies) and a cellular immune response (e.g., cytotoxic T cells (CTLs)).

The present invention also provides a method for eliciting an immune response to an HIV infection in a mammal which is prophylactic for an HIV infection, the method comprising administering to a mammal a vaccine composition comprising a polyenv vaccine of the present invention, which is protective for the mammal against a clinical HIV-related pathology caused by infection of at least one HIV strain.

The present invention also provides a method for eliciting an immune response to an HIV infection in a mammal for therapy of an HIV infection. The method comprises administering to a mammal a composition comprising an inactivated or attenuated polyenv vaccine of the present invention, which composition elicits an enhanced immune response, relative to controls, in the mammal against a clinical virus pathology caused by infection with at least one HIV strain.

Other objects, features, advantages, utilities and embodiments of the present invention will be apparent to skilled practitioners from the following detailed description and examples relating to the present invention.

DETAILED DESCRIPTION OF THE DISCLOSURE

Figure 1:
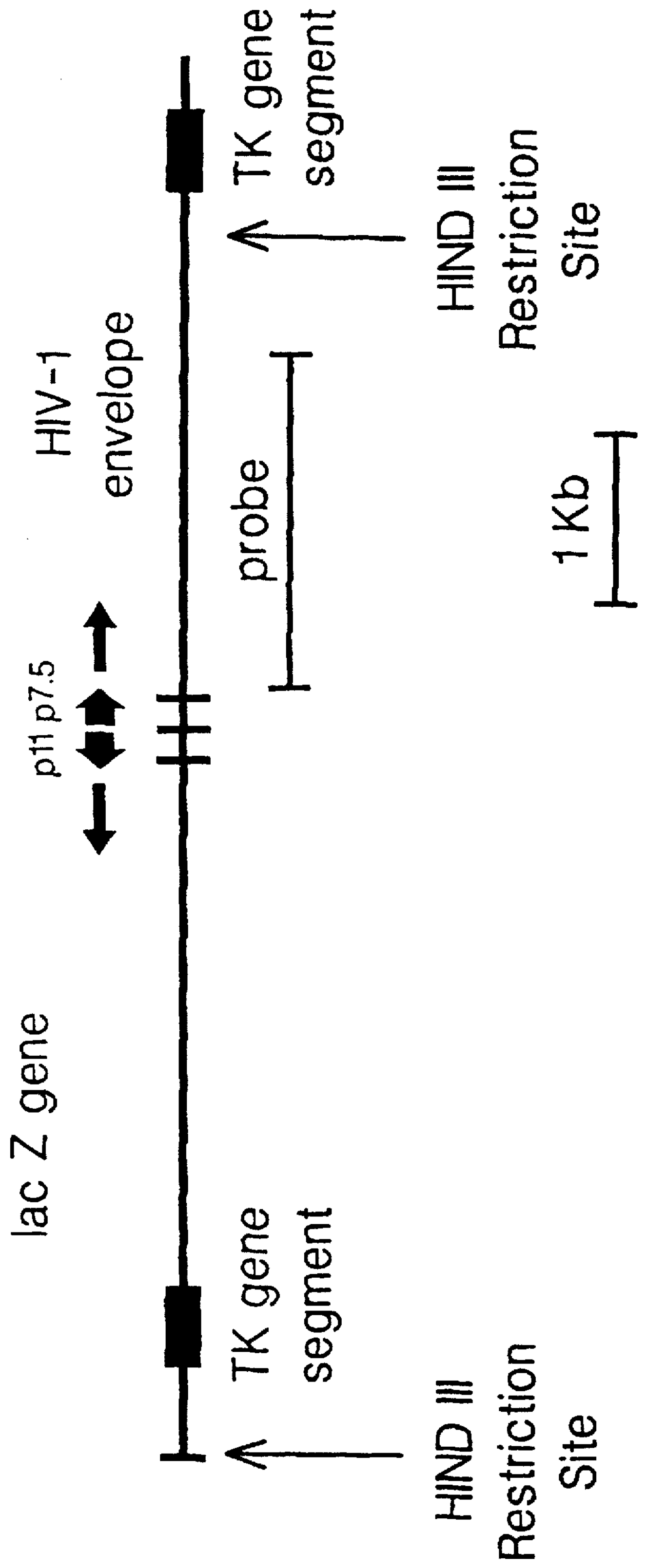
FIG. 1 is a schematic representation of the orientation of the HIV-1 gene in a vaccinia virus genome. The HIV-1 envelope gene is positioned between right and left segments of the thymidine kinase locus. A HindIII site exists at the C-terminus of the HIV-1 envelope gene. The appropriate insertion yields a HindIII fragment of approximately 7 kb in size. Southern blots with this pattern confirmed the position and correct orientation of the HIV-1 envelope gene.

Discovery of Unexpectedly Enhanced Immune Responses to Mixed HIV Polyenv Vaccines Previous attempts to provide vaccines against different strains of HIV have focused on one or more variable regions of gp 120 or gp 160. It was expected that such variable regions, provided in a vaccine, would provide broad protection against HIV infection. However, such vaccines have not been successful, where the vaccine-induced immune response does not recognize many different strains of HIV. Therefore, a critical need exists to provide vaccines that elicit immune responses to multiple strains of HIV, such that the vaccines are suitable for treatment and/or prevention of HIV.

The present inventors have discovered that unexpectedly enhanced immune responses can be induced against several or many different HIV strains, by the use of polyenv vaccines that contain a mixture of at least 4–40, up to as many as 10,000, recombinant vaccinia viruses that each encode a different envelope protein variant (EPV). The vaccine can also contain EPVs expressed by the vaccinia viruses, e.g., as produced in the host cells used for the virus production.

This immune response (as humoral and/or cellular) is found to be effective for a broader range of strains of an infectious virus, such as HIV, and is not limited to the virus strains expressing the specific envelope protein variants (EPVs) provided by the polyenv vaccine. The present invention thus provides multiple EPVs encoded by a recombinant viral vaccine which give unexpectedly enhanced immune responses to multiple strains of HIV.

The EPV encoding nucleic acid (envelope variant (EV) nucleic acid) can be isolated from the same or different population (e.g., geographic) of humans infected with HIV. Alternatively, the different EV nucleic acids can be obtained from any source and selected based on screening of the sequences for differences in coding sequence or in elicited humoral and/or cellular immune responses to multiple HIV strains, in vitro or in vivo, according to known methods.

Polyenv Vaccines and Envelope Protein Variants

The present invention thus provides, in one aspect, polyenv vaccines using mixtures of at least 4–40, and up to 10,000, different recombinant vaccinia viruses that each express a different envelope protein variant, or an antigenic portion thereof. Also provided are methods of making and using such polyenv vaccines A polyenv vaccine of the present invention induces at least one of a humoral and a cellular immune response in a mammal who has been administered the polyenv vaccine, but the response to the vaccine is subclinical, or is effective in enhancing at least one immune response to at least one strain of HIV, such that the vaccine administration is suitable for vaccination purposes.

An EPV, encoded by a recombinant vaccinia virus alternatively includes polypeptides having immunogenic activity elicited by an amino acid sequence of an EPV amino acid sequence as at least one epitope or antigenic determinant. This amino acid sequence substantially corresponds to at least one 10–900 amino acid fragment and/or consensus sequence of a known HIV EPV. Such an EPV can have overall homology or identity of at least 50% to a known envelope protein amino acid sequence, such as 50–99% homology, or any range or value therein, while eliciting an immunogenic response against at least one strain of an HIV.

Percent homology can be determined, for example, by comparing sequence information using the GAP computer program, version 6.0, available from the University of Wisconsin Genetics Computer Group (UWGCG). The GAP program utilizes the alignment method of Needleman and Wunsch (*J. Mol. Biol.* 48:443 (1970), as revised by Smith and Waterman (*Adv. Appl. Math.* 2:482 (1981)). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unitary comparison matrix (containing a value of 1 for identities and 0 for non-identities) and the weighted comparison matrix of Gribskov and Burgess, *Nucl. Acids Res.* 14:6745 (1986), as described by Schwartz and Dayhoff, eds., *Atlas of Protein Sequence and Structure*, National Biomedical Research Foundation, Washington, D.C. (1979), pp. 353–358; (2) a penalty of 3.0 for each gap and an additional 0.10 penalty for each symbol in each gap; and (3) no penalty for end gaps.

In a preferred embodiment, an EPV of the present invention is a variant form of at least one HIV envelope protein. Preferably, the EPV includes gp120 and the oligomerization domain of gp41, as gp140 (Hallenberger, et al., *Virology* 193:510–514 (1993), entirely incorporated herein by reference).

Known HIV envelope proteins contain about 750 to 900 aminio acids. Examples of such sequences are readily available from commercial and institutional HIV sequence databases, such as GENBANK, or as published compilations, such as Myers et al., eds., *Human Retroviruses and AIDS, A Compilation and Analysis of Nucleic Acid and Amino Acid Sequences*, Vol. I and II, Theoretical Biology and Biophysics, Los Alamos, N. Mex. (1993). Substitutions or insertions of an EPV to obtain an additional EPV, encoded by a nucleic acid for use in a recombinant vaccinia virus or polyenv vaccine of the present invention, can include substitutions or insertions of at least one amino acid residue (e.g., 1–25 amino acids). Alternatively, at least one amino acid (e.g., 1–25 amino acids) can be deleted from an EPV sequence. Preferably, such substitutions, insertions or deletions are identified based on sequence determination of envelope proteins obtained by nucleotide sequencing of at least one EPV encoding nucleic acid from an individual infected with HIV.

Non-limiting examples of such substitutions, insertions or deletions preferably are made by the amplification of env DNA or RNA sequences from HIV-1 infected patients, which can be determined by routine experimentation to provide modified structural and functional properties of an envelope protein or an EPV. The EPVs so obtained preferably have different antigenic properties from the original EPV. Such antigenic differences can be determined by suitable assays, e.g., by testing with a panel of monoclonal antibodies specific for HIV envelope proteins in an ELISA assay.

Any substitution, insertion or deletion can be us&d as long as the resulting EPV protein elicits antibodies which bind to HIV envelope proteins, but which EPV has a different pattern than antibodies elicited by a second EPV. Each of the above substitutions, insertions or deletions can also include modified or unusual amino acid, e.g., as provided in 37 C.F.R. § 1.822(*p*)(2), which is incorporated herein by reference.

The following Table 1 presents non-limiting examples of alternative variants of envelope proteins of HIVs, that can be encoded by a recombinant vaccinia virus according to present invention.

TABLE 1

HIV Envelope Protein Variants

| | 1 | 2 | 3 | 4 | 5 | 6 | 7 | 8 | 9 | 10 | 1 | 2 | 3 | 4 | 5 | 6 | 7 | 8 | 9 | 20 | 1 | 2 | 3 | 4 | 5 | 6 | 7 | 8 | 9 | 30 |
|---|---|---|---|---|---|---|---|---|---|---|---|---|---|---|---|---|---|---|---|---|---|---|---|---|---|---|---|---|---|---|
| 1 | E | K | E K | Q | K | T | V M | A | M | R K T I | V A | K M T R | E G M | S T I M K | Q R K G E | M R K G T | K N S E | K C Y W D | Q P N R W | H N C R Q | L W R K S | W L K | R K G I S | W I K | G | W T | R K M | W G L T I | G Y L T | T I M Y |
| | 1 | 2 | 3 | 4 | 5 | 6 | 7 | 8 | 9 | 40 | 1 | 2 | 3 | 4 | 5 | 6 | 7 | 8 | 9 | 50 | 1 | 2 | 3 | 4 | 5 | 6 | 7 | 8 | 9 | 60 |
| 31 | M L A I | L I M A T | L F A M I | G W I L A | L I M T | M I T P | I T P C | C S L | S L | | A V G I N | T V A E K | E S Q D V | K Q D N | L | W Y | V A | T | V | Y | Y S A | G | V I | P | V I | W | K E H | E D | A | T E V N A |
| | 1 | 2 | 3 | 4 | 5 | 6 | 7 | 8 | 9 | 70 | 1 | 2 | 3 | 4 | 5 | 6 | 7 | 8 | 9 | 80 | 1 | 2 | 3 | 4 | 5 | 6 | 7 | 8 | 9 | 90 |
| 61 | T P | T V | L | F | C | A | S | D E | A R | K R N | A T S L | Y H T | D S K A E | T R A K P | E | V A R Q K | H | N K | V I | W C | A | T S K | H Y Q | A | C | V | P | T | D N G | P |
| | 1 | 2 | 3 | 4 | 5 | 6 | 7 | 8 | 9 | 100 | 1 | 2 | 3 | 4 | 5 | 6 | 7 | 8 | 9 | 110 | 1 | 2 | 3 | 4 | 5 | 5 | 7 | 8 | 9 | 120 |
| 91 | N D S T | P | Q H R Y | E | V I L M F | V L Y D S | L M | V G E P | N S | V | T G | E E D | N K D H | F D | N I | M | W R | K T | N N | D I S Y | M | V D | E N | Q | M Q | H T | E | D V | I | I |
| | 1 | 2 | 3 | 4 | 5 | 6 | 7 | 8 | 9 | 130 | 1 | 2 | 3 | 4 | 5 | 6 | 7 | 8 | 9 | 140 | 1 | 2 | 3 | 4 | 5 | 6 | 7 | 8 | 9 | 150 |
| 121 | S N | L | W | D E | Q E | S | L | K | P | C | V E | K V Q | L M | T | P L | L C | C V | V | S T N Q | L M | K N D S I | C | T K I H G | D H N Q K | L V Y W F | K T G R L | N T | D A G | T S M | N E T I S |
| | 1 | 2 | 3 | 4 | S | 6 | 7 | 8 | 9 | 160 | 1 | 2 | 3 | 4 | 5 | 6 | 7 | 8 | 9 | 170 | 1 | 2 | 3 | 4 | 5 | 6 | 7 | 8 | 9 | 180 |
| 151 | T N I | S K E | N S | N S | V K | T | S T N | S T V G | S K T | W N I S L | G W S Q | R K K W G | N R E V T | I E K | M I T I V | E D G | E R Q G N | G E A S K | E K G R L | I M V R | K T R Q | N K | C | S P T E | F Y | N K Y Q | I V Q M T | S T | T K P | S G N I E |

TABLE 1-continued

HIV Envelope Protein Variants

| | 1 | 2 | 3 | 4 | 5 | 6 | 7 | 8 | 9 | 190 | 1 | 2 | 3 | 4 | 5 | 6 | 7 | 8 | 9 | 200 | 1 | 2 | 3 | 4 | 5 | 6 | 7 | 8 | 9 | 210 |
|---|---|---|---|---|---|---|---|---|---|---|---|---|---|---|---|---|---|---|---|---|---|---|---|---|---|---|---|---|---|---|
| 181 | I L V R K | R G K S T | G D N | K R Q E | V I M K Q | Q K H E | K Q R T | E D V A G | Y N R S H | A S T | F L Y T H | F L | Y R H N | K N R T V | L H T P S | D | I V L | I V A M S | F Q K E N | I V L | D K G E N | K D N G | G S | N D | D I | S N | P | K | N D T S | D A S |
| | 1 | 2 | 3 | 4 | 5 | 6 | 7 | 8 | 9 | 220 | 1 | 2 | 3 | 4 | 5 | 6 | 7 | 8 | 9 | 230 | 1 | 2 | 3 | 4 | 5 | 6 | 7 | 8 | 9 | 240 |
| 211 | T S S | T S | T N | N I | T A | S N | Y | K T R G | W N | F K Y | T R I K M | L I | T I | S H N T | C | N S D | T R S | S T | V T A I | I V L | T K | Q | A | C | P S | K | V I T | S T | F | E Q D |
| | 1 | 2 | 3 | 4 | 5 | 6 | 7 | 8 | 9 | 250 | 1 | 2 | 3 | 4 | 5 | 6 | 7 | 8 | 9 | 260 | 1 | 2 | 3 | 4 | 5 | 6 | 7 | 8 | 9 | 270 |
| 241 | P | I | P F | I M | H | Y F H | C | A T | P G | A T | G | F Y | A V | I M L | L F | K | C | N K R | N D S | K A P E T | T K E C Q | F | N S E | G | T K S | G E | P Q S T I | C | T K H S R | N |
| | 1 | 2 | 3 | 4 | 5 | 6 | 7 | 8 | 9 | 280 | 1 | 2 | 3 | 4 | 5 | 6 | 7 | 8 | 9 | 290 | 1 | 2 | 3 | 4 | 5 | 6 | 7 | 8 | 9 | 300 |
| 271 | V I | S T | T S V | V R | Q T H | C | T | H | G | I | R K S | P | V I T | V | S T | T | Q H | L | L | L I S | N | G | S T | L | A S | E K R | E G K R | E G R K D | V I D G | V K R I M |
| | 1 | 2 | 3 | 4 | 5 | 6 | 7 | 8 | 9 | 310 | 1 | 2 | 3 | 4 | 5 | 6 | 7 | 8 | 9 | 320 | 1 | 2 | 3 | 4 | 5 | 6 | 7 | 8 | 9 | 330 |
| 301 | I L V M | R M | S G A V | A D E S K | N D | F I L P K | T S M A L | D N E | N S G | A V T G H | K R D | T I N V | I W | I L V | V A | Q H T | L | N K T | Q E A D T | S P T A | V I L | E A Q V T | I V | N V T M | C Y | T I A E H | R | P E | N S A E H | N I K Y Q |
| | 1 | 2 | 3 | 4 | 5 | 6 | 7 | 8 | 9 | 340 | 1 | 2 | 3 | 4 | 5 | 6 | 7 | 8 | 9 | 350 | 1 | 2 | 3 | 4 | 5 | 6 | 7 | 8 | 9 | 360 |
| 331 | N K Y T S | T V K R I | R N S P V | K R G Q | S R N T G | I | R Y Y H P | H K | I R M L S | Q H P Y | R I S | G A | F P S L | G K R M | R Q K M | A V T S W | F I W V Y | V H Y F I | T A V R N | I T R L M | G R K D E | K R Q D A | I K S G V | L I R V A | G S A F N | N D N T I | M I L S T | R G | Q K L R V | A |

TABLE 1-continued

HIV Envelope Protein Variants

| | 1 | 2 | 3 | 4 | 5 | 6 | 7 | 8 | 9 | 370 | 1 | 2 | 3 | 4 | 5 | 6 | 7 | 8 | 9 | 380 | 1 | 2 | 3 | 4 | 5 | 6 | 7 | 8 | 9 | 390 |
|---|---|---|---|---|---|---|---|---|---|---|---|---|---|---|---|---|---|---|---|---|---|---|---|---|---|---|---|---|---|---|
| 361 | H<br>Y | C | N<br>K<br>T | I<br>L<br>V<br>Y | S<br>A<br>N | R<br>G<br>K<br>E<br>A | A<br>E<br>T<br>R<br>S | K<br>Q<br>D<br>N<br>A | W | N<br>K<br>S<br>E<br>F | N<br>A<br>K<br>R<br>D | T<br>V<br>A<br>I | L<br>I<br>V | K<br>E<br>Q<br>S<br>N | Q<br>G<br>K<br>R<br>L | I<br>V<br>L<br>T | D<br>V<br>A | S<br>K<br>T<br>E<br>R | K<br>S<br>Q<br>H<br>I | L<br>Y | R<br>K<br>Q<br>G<br>I | E<br>K<br>A<br>V<br>D | Q<br>K<br>H<br>R | F<br>Y<br>L<br>S | G<br>K<br>D | N<br>D | N | K<br>Q<br>H | T<br>S | I<br>V<br>T<br>M |
| | 1 | 2 | 3 | 4 | 5 | 6 | 7 | 8 | 9 | 400 | 1 | 2 | 3 | 4 | 5 | 6 | 7 | 8 | 9 | 410 | 1 | 2 | 3 | 4 | 5 | 6 | 7 | 8 | 9 | 420 |
| 391 | I<br>V<br>N<br>A<br>K | F<br>S<br>L | K<br>N<br>T<br>A<br>S | Q<br>H<br>S<br>K<br>N | S<br>H<br>P<br>G<br>T | S<br>A | G<br>C | G<br>C | D | P<br>L<br>I<br>V<br>Q | E | I<br>V | V<br>T<br>S | T<br>M<br>L<br>H | H<br>Y<br>L | S<br>N<br>T<br>M<br>H | F<br>L | N<br>I<br>T | C<br>V | G<br>R<br>V<br>W<br>E | G | E<br>D | F<br>I | F | Y | C | N<br>D | S<br>T<br>A | T<br>S<br>A<br>R | Q<br>G<br>N<br>P<br>K |
| | 1 | 2 | 3 | 4 | 5 | 6 | 7 | 8 | 9 | 430 | 1 | 2 | 3 | 4 | 5 | 6 | 7 | 8 | 9 | 440 | 1 | 2 | 3 | 4 | 5 | 6 | 7 | 8 | 9 | 450 |
| 421 | L<br>M<br>I | F<br>D | N<br>S<br>D<br>T | S<br>N<br>T<br>G<br>A | T<br>I | W<br>Y<br>C<br>F | F<br>R<br>N<br>S<br>G | N<br>L | S<br>N<br>V<br>D | T<br>K<br>G<br>S | W<br>A<br>D<br>K<br>M | S<br>G<br>D<br>K | T<br>I<br>P<br>N<br>G | K<br>E<br>I<br>T | G<br>W<br>K<br>C<br>M | S<br>N<br>D<br>G<br>L | N<br>S<br>G<br>T<br>D | N<br>G<br>D<br>S<br>I | T<br>M<br>G<br>N<br>Q | E<br>K<br>G<br>Q | G<br>E<br>R<br>A<br>S | S<br>N<br>E<br>R<br>K | D<br>N<br>G<br>E<br>R | T<br>N<br>P<br>L<br>S | I<br>L<br>V | T<br>I<br>V<br>K | L<br>H<br>I | P<br>Q<br>L<br>D | C | R<br>K |
| | 1 | 2 | 3 | 4 | 5 | 6 | 7 | 8 | 9 | 460 | 1 | 2 | 3 | 4 | 5 | 6 | 7 | 8 | 9 | 470 | 1 | 2 | 3 | 4 | 5 | 6 | 7 | 8 | 9 | 480 |
| 451 | I | K | Q<br>E | I<br>F | I<br>V | N<br>R<br>K | M<br>I<br>R<br>S<br>L | W | Q<br>A | E<br>G<br>R<br>K<br>V | V<br>T<br>A | G<br>R | K<br>Q<br>R | A<br>S | M<br>T<br>L<br>I | Y | A<br>D | P<br>L | P | I<br>F<br>T | S<br>G<br>Q<br>K<br>E | G<br>R | Q<br>V<br>E<br>T<br>L | I<br>L | R<br>S<br>K<br>T | C<br>F | S<br>I<br>E<br>V<br>T | S | N | I |
| | 1 | 2 | 3 | 4 | 5 | 6 | 7 | 8 | 9 | 490 | 1 | 2 | 3 | 4 | 5 | 6 | 7 | 8 | 9 | 500 | 1 | 2 | 3 | 4 | 5 | 6 | 7 | 8 | 9 | 510 |
| 481 | T | G | L<br>T<br>I | L<br>I | L | T<br>V<br>E | R<br>S | D | G<br>S | G<br>V | A<br>T<br>E<br>D<br>G | N<br>D<br>S<br>G<br>E | E<br>Q<br>K<br>T<br>D | N<br>T<br>S<br>A<br>K | N<br>S<br>A<br>K | E<br>D<br>G<br>R<br>T | S<br>T<br>E<br>N<br>I | E<br>V<br>N<br>L | I<br>V<br>T | F<br>I<br>L | R<br>S | P<br>L | G<br>T<br>A<br>V<br>I | G | G<br>N | D<br>I<br>E | M<br>K | R<br>N | D<br>I | N |
| | 1 | 2 | 3 | 4 | 5 | 6 | 7 | 8 | 9 | 520 | 1 | 2 | 3 | 4 | 5 | 6 | 7 | 8 | 9 | 530 | 1 | 2 | 3 | 4 | 5 | 6 | 7 | 8 | 9 | 540 |
| 511 | W<br>R | R<br>I | S<br>N<br>T | E<br>K | L | Y<br>F | K<br>N | Y | K | V<br>D | V<br>I | K<br>R<br>T<br>Q<br>E | I<br>V | E<br>K | P<br>L<br>T | L<br>I<br>F | G<br>S | V<br>I | A | P | T<br>S | K<br>R | A<br>S<br>P<br>M<br>I | K<br>R<br>S<br>A | R | R<br>P<br>H | V<br>I | V<br>M<br>I | Q<br>E<br>A<br>W<br>H | R |

TABLE 1-continued

HIV Envelope Protein Variants

| | 1 | 2 | 3 | 4 | 5 | 6 | 7 | 8 | 9 | 550 | 1 | 2 | 3 | 4 | 5 | 6 | 7 | 8 | 9 | 560 | 1 | 2 | 3 | 4 | 5 | 6 | 7 | 8 | 9 | 570 |
|---|---|---|---|---|---|---|---|---|---|---|---|---|---|---|---|---|---|---|---|---|---|---|---|---|---|---|---|---|---|---|
| 541 | E<br>K<br>Q | K<br>E | R | A | V<br>I<br>A | G<br>F<br>V | E<br>I<br>T<br>A<br>L | I<br>V<br>L<br>M | G | A<br>V<br>M | L<br>M<br>V<br>F<br>I | F<br>S<br>L<br>I | L<br>I<br>P | G | F<br>V | L | G<br>S | A | A | G<br>S | S | T | M | G<br>A | A | A<br>V<br>R<br>G<br>T | S<br>A<br>P | M<br>L<br>I<br>V<br>T | T<br>A | L<br>V |
| | 1 | 2 | 3 | 4 | 5 | 6 | 7 | 8 | 9 | 580 | 1 | 2 | 3 | 4 | 5 | 6 | 7 | 8 | 9 | 590 | 1 | 2 | 3 | 4 | 5 | 6 | 7 | 8 | 9 | 600 |
| 571 | T<br>A | V<br>G | Q<br>R<br>P | A<br>T<br>P<br>L | R<br>H | Q<br>H<br>L<br>K<br>S | L<br>V | L<br>M | S<br>K | G<br>D | I | V | Q<br>H | Q | Q | N<br>S<br>D | N | L | L | R<br>M<br>R | A | I | E<br>K<br>D<br>Q | A<br>G | Q | Q | H<br>Q | L<br>M | L | Q<br>K<br>E<br>R |
| | 1 | 2 | 3 | 4 | 5 | 6 | 7 | 8 | 9 | 610 | 1 | 2 | 3 | 4 | 5 | 6 | 7 | 8 | 9 | 620 | 1 | 2 | 3 | 4 | 5 | 6 | 7 | 8 | 9 | 630 |
| 601 | L | T<br>S | V<br>I | W | G | I<br>V | K<br>R | Q | L | Q<br>R | A<br>L<br>T | R | I<br>V<br>L | L<br>Q | A | V<br>L<br>I | E | R<br>T<br>S | Y<br>F<br>L | L<br>I | K<br>R<br>Q<br>G | D<br>E<br>N | Q | Q<br>R<br>K | L<br>R<br>I | L<br>M | G<br>E<br>R<br>S<br>N | I<br>F<br>M<br>N<br>L | W<br>L | G<br>W |
| | 1 | 2 | 3 | 4 | 5 | 6 | 7 | 8 | 9 | 640 | 1 | 2 | 3 | 4 | 5 | 6 | 7 | 8 | 9 | 650 | 1 | 2 | 3 | 4 | 5 | 6 | 7 | 8 | 9 | 660 |
| 631 | C<br>R | S<br>K | G | K<br>R | L<br>T<br>H<br>I<br>A | I<br>V | C | T<br>P<br>Y | T | A<br>T<br>N<br>F<br>S | V | P<br>K | W | N | A<br>S<br>F<br>N | S<br>T<br>A | W | S<br>G<br>S | N<br>R | K<br>R<br>Y | S<br>T<br>N<br>G | L<br>M<br>Q<br>V<br>R | E<br>D<br>N<br>S<br>K | Q<br>D<br>M<br>S<br>K | I<br>F | W | N<br>D<br>G<br>Q<br>W | N<br>K<br>H<br>T | M<br>T<br>L<br>N | T<br>M |
| | 1 | 2 | 3 | 4 | 5 | 6 | 7 | 8 | 9 | 670 | 1 | 2 | 3 | 4 | 5 | 6 | 7 | 8 | 9 | 680 | 1 | 2 | 3 | 4 | 5 | 6 | 7 | 8 | 9 | 690 |
| 661 | W | M<br>L<br>I<br>Q | E<br>Q<br>K | W | D<br>E | R<br>K<br>Q | E<br>L<br>H<br>Q | I<br>V | N<br>D<br>E<br>S | N<br>S<br>K | Y<br>V<br>I | T<br>S | S<br>N<br>G<br>D<br>K | L<br>T<br>I<br>V<br>E | I | H<br>Y<br>F | S<br>T<br>N | L<br>I<br>E | I<br>L | E<br>T<br>Q | E<br>D<br>Q<br>N | S<br>A | Q<br>A | N<br>I<br>T<br>D<br>V | Q | Q | E<br>G<br>D | K<br>I<br>Q<br>R | N | E<br>Q<br>V |
| | 1 | 2 | 3 | 4 | 5 | 6 | 7 | 8 | 9 | 700 | 1 | 2 | 3 | 4 | 5 | 6 | 7 | 8 | 9 | 710 | 1 | 2 | 3 | 4 | 5 | 6 | 7 | 8 | 9 | 720 |
| 691 | Q<br>L<br>R<br>K | E<br>D<br>A<br>K | L | L | E<br>G<br>A<br>K<br>Q | L | D<br>N | K<br>E<br>S<br>Q | W | A<br>T<br>K | S<br>N<br>G | L | W | N<br>S | W | F<br>S<br>Y<br>L | N<br>S<br>G<br>D | I | T<br>S | N<br>Q<br>K | W | L | W | Y<br>S | I | K<br>R | L<br>I | F<br>A | I<br>V | M<br>I |

TABLE 1-continued

HIV Envelope Protein Variants

| | 1 | 2 | 3 | 4 | 5 | 6 | 7 | 8 | 9 | 730 | 1 | 2 | 3 | 4 | 5 | 6 | 7 | 8 | 9 | 740 | 1 | 2 | 3 | 4 | 5 | 6 | 7 | 8 | 9 | 750 |
|---|---|---|---|---|---|---|---|---|---|---|---|---|---|---|---|---|---|---|---|---|---|---|---|---|---|---|---|---|---|---|
| 721 | I V A | V I | G A | G A | L I | V I | G | L V | R K | I V | V I | F M | A S T I | V I | L F | S C N | V I L | V I | N K R | R S N | V F I | R S N | Q A | G | Y | S Q | P | L | S | F L |
| | 1 | 2 | 3 | 4 | 5 | 6 | 7 | 8 | 9 | 760 | 1 | 2 | 3 | 4 | 5 | 6 | 7 | 8 | 9 | 770 | 1 | 2 | 3 | 4 | 5 | 6 | 7 | 8 | 9 | 780 |
| 751 | Q | T I | H R L P | L T A P F | P H N I | I V T A G | P Q T R S | R E G Q | G E | P L A | D G E | R Q T | P L Q | E D G | G R E | I T | E D | E G | E G | G | G | E D | R Q G E | D G | R K | D G P S | R T G K | S W | I V G N S | R G Q P A |
| | 1 | 2 | 3 | 4 | 5 | 6 | 7 | 8 | 9 | 790 | 1 | 2 | 3 | 4 | 5 | 6 | 7 | 8 | 9 | 800 | 1 | 2 | 3 | 4 | 5 | 6 | 7 | 8 | 9 | 810 |
| 781 | L A S | V L P | N D H T S | G | S F L C | L S | A T P Q | L Q | I F L | W Y | D E V G T | D | L C | R W G | S T N A | L C I | C F I G | L S I | F S W | S C L T | Y | H R Q | R L S | L | R T S | D N S | L F C | L A I | L S C | I T V Q H |
| | 1 | 2 | 3 | 4 | 5 | 6 | 7 | 8 | 9 | 820 | 1 | 2 | 3 | 4 | 5 | 6 | 7 | 8 | 9 | 830 | 1 | 2 | 3 | 4 | 5 | 6 | 7 | 8 | 9 | 840 |
| 811 | V A I | T A V K M | R K | I T A L V | V I L | E D S K | L I T Y | L | G K R | R H L | R G L | G L I | W L | E D N | A G I V R | L I C | K R | Y L I | W L C G | W G A | N S A C | L V | L V M T | Q L I | Y | W I | S K G T L | Q R | E | L |
| | 1 | 2 | 3 | 4 | 5 | 6 | 7 | 8 | 9 | 850 | 1 | 2 | 3 | 4 | 5 | 6 | 7 | 8 | 9 | 860 | 1 | 2 | 3 | 4 | 5 | 6 | 7 | 8 | 9 | 870 |
| 841 | K R Q | N I S | S | A V F | V I S T | S N | L W F | L F V | N D A | A T | T I V L | A | I V | A V S | V | A T | E G N | G E R W | T | D | R G K | V I A | I | E L A | V I G A | V A | Q R | G R A T | A I T V F | Y C L G V |
| | 1 | 2 | 3 | 4 | 5 | 6 | 7 | 8 | 9 | 880 | 1 | 2 | 3 | 4 | 5 | 6 | 7 | 8 | 889 | | | | | | | | | | | |
| 871 | R Q T | A G I | I F V | R L I | H N | I V | P H | R T | R | I V | R | Q | G | L F A | E K | R G | I L A R S | L | L Q V | | | | | | | | | | | |

Accordingly, based on the above examples of specific substitutions, alternative substitutions can be made by routine experimentation, to provide alternative EPVs of the present invention, e.g., by making one or more substitutions, insertions or deletions in envelope proteins or EPV's which give rise to differential immune responses.

Amino acid sequence variations in an EPV of the present invention can be prepared e.g., by mutations in the DNA. Such EPVs include, for example, deletions, insertions or substitutions of nucleotides coding for different amino acid residues within the amino acid sequence. Obviously, mutations that will be made in nucleic acid encoding an EPV must not place the sequence out of reading frame and preferably will not create complementary domains that could produce secondary mRNA structures (see, e.g., Ausubel (1995 rev.), infra; Sambrook (1989), infra).

EPV-encoding nucleic acid of the present invention can also be prepared by amplification or site-directed mutagenesis of nucleotides in DNA or RNA encoding an envelope protein or an EPV, and thereafter synthesizing or reverse transcribing the encoding DNA to produce DNA or RNA encoding an EPV(see, e.g., Ausubel (1995 rev.), infra; Sambrook (1989), infra), based on the teaching and guidance presented herein.

Recombinant vaccinia viruses expressing EPV's of the present invention, or nucleic acid encoding therefor, include a finite set of EPV-encoding sequences as substitution nucleotides that can be routinely obtained by one of ordinary skill in the art, without undue experimentation, based on the teachings and guidance presented herein. For a detailed description of protein chemistry and structure, see Schulz, G. E. et al., *Principles of Protein Structure*, Springer-Verlag, New York, N.Y. (1978), and Creighton, T.E., *Proteins: Structure and Molecular Properties*, W. H. Freeman & Co., San Francisco, Calif. (1983), which are hereby incorporated by reference. For a presentation of nucleotide sequence substitutions, such as codon preferences, see Ausubel et al., eds. *Current Protocols in Molecular Biology*, Greene Publishing Assoc., New York, N.Y. (1987, 1988, 1989, 1990, 1991, 1992, 1993, 1994, 1995)(hereinafter, "Ausubel (1995 rev.)") at §§ A.1.1–A.1.24, and Sambrook, J. et al., *Molecular Cloning: A Laboratory Manual*, Second Edition, Cold Spring Harbor Laboratory Press, Cold Spring Harbor, N.Y. (1989) at Appendices C and D.

Thus, one of ordinary skill in the art, given the teachings and guidance presented herein, will know how to substitute other amino acid residues in other positions of an env DNA or RNA to obtain alternative EPVs, including substitutional, deletional or insertional variants.

Screening Assays for HIV Activity

For screening HIV activity of an EPV encoding recombinant vaccinia virus, any known and/or suitable screening assay can be used, as is known in the art. For example, known HIV assays include viral infectivity assays (see, e.g., Chesebro et al., *J. Virol.* 62:3779–3788 (1988); Aldovini et al., eds., *Techniques in HIV Research* pp. 71–76 (1990)); neutralization assays (see, e.g., Golding et al., *AIDS Res. Hum. Retrovir:* 10:633–643 (1994); Hanson., *AIDS Res. Hum. Retrovir.* 10:645–648 (1994); Laal et al., *Res. Hum. Retrovir.* 9:781–785 (1993); Hanson, *J. Acquit. Immune Defic. Syndr.* 7:211–219 (1994)); peripheral mononuclear (PMN) cell assays (see, e.g., Arduino et al., *Antimicrob. Agents Chermother.* 37:1095–1101 (1990)); and cytotoxic T-lymphocyte (CTL) assays (see, e.g., Hammond et al., *J. Exp. Med.* 176:1531–1542 (1992); McElrath et al., *J. Virol.* 68:5074–5083 (1994); Walker et al., *Cell Immunol.* 119:470–475 (1989); Weinhold et al., *AIDS Res. Hum. Retrovir.* 8:1373 (1992)). Other suitable activities, alone or in any combination, include, but are not limited to, quantitative and/or qualitative measurement of transcription, replication, translation, virion incorporation, virulence, viral yield, and/or morphogenesis. The above references are entirely incorporated herein by reference.

Recombinant Vaccinia Virus Encoding EPV's, Polyenv Vaccines and Methods of Making and Using Thereof Overview. Recombinant vaccinia viruses (VV) expressing HIV envelope proteins (e.g., gp41, gp120 and/or gp160, or a portion thereof) provide materials useful for the production and testing of mixed vaccines that induce at least one of a humoral or cellular immune response against the virus, as well as for analyses of B-cell and CTL determinants.

A polyenv vaccine of the present invention consists of a mixture of n distinct recombinant vaccinia viruses, where n is a whole number from about 4 to about 10,000 (or any range or value therein), wherein each vaccinia vector construct expresses a variant of a HIV-1 envelope protein (EPV) (e.g., gp41, gp 120 or gp160). The recombinant vaccinia virus functionally encodes an EPV and is prepared by recombination of wildtype VV with a plasmid. Multiple, distinct plasmids encoding EPV can be prepared by substituting one EPV encoding sequence with another, e.g., using a restriction fragment or mutagenesis.

Preparation of Recombinant Vaccinia Viruses. Methods for the preparation of individual plasmids (each expressing a unique HIV protein sequence) can utilize DNA or RNA amplification for the substitution of isolated envelope protein variant sequences into a vector (e.g., pVenv4 or pVenv1 (Hallenberger et at., *Virology* 193:510–514 (1993)), which vector encodes a known HIV envelope protein sequence (e.g., available from the NIAID AIDS Research & Reference Reagent Program, Rockville, Md.).

Methods of amplification of RNA or DNA are well known in the art and can be used according to the present invention without undue experimentation, based on the teaching and guidance presented herein. Known methods of DNA or RNA amplification include, but are not limited to polymerase chain reaction (PCR) and related amplification processes (see, e.g., U.S. Pat. Nos. 4,683,195, 4,683,202, 4,800,159, 4,965,188, to Mullis et al.; 4,795,699 and 4,921,794 to Tabor et al; 5,142,033 to Innis; 5,122,464 to Wilson et al.; 5,091, 310 to Innis; 5,066,584 to Gyllensten et al; 4,889,818 to Gelfand et al; 4,994,370 to Silver et al; 4,766,067 to Biswas; 4,656, 134 to Ringold) and RNA mediated amplification which uses anti-sense RNA to the target sequence as a template for double stranded DNA synthesis (U.S. Pat. No. 5,130,238 to Malek et al. with the trade name NASBA), the entire contents of which patents are herein entirely incorporated by reference.

For example, recombinant vaccinia virus constructs prepared by this route can be used for immunizations and elicitation of HIV-specific T and/or B-cell responses. Primers utilize conserved HIV sequences and thus successfully amplify env genes from many diverse HIV-1 patient samples. The basic techniques described here can similarly be used with PCR or other types of amplification primers, in order to substitute smaller or larger pieces of the env sequence from field isolates for that found in vectors encoding an HIV envelope protein. See, e.g., Ausubel; infra, Sambrook, infra.

EPV Encoding Nucleic Acids. The technique begins with the isolation of DNA from HIV infected cells and the amplification of env sequences by PCR. PCR or other amplification products provide the simplest means for the isolation of HIV sequences, but any other suitable and known methods can be used such as cloning and isolation of EPV encoding nucleic acid or proteins (see Ausubel, infra; Sambrook, infra). Enzyme restriction sites are preferably incorporated into PCR or other amplification primer sequences to facilitate gene cloning.

Isolated DNA for PCR can be prepared from multiple virus sources, inclusive of fresh or frozen whole blood from HIV+ patients and cells that have been infected in vitro with virus isolates.

In order to produce new HIV env constructs, the polymerase chain reaction (PCR) is preferably used to amplify 100–2700 base pairs (bp) of an env gene from each different HIV patient sample. The PCR primers can represent well-conserved HIV sequences which are suitable for amplifying env genes from known samples of env genes, isolated HIVs or diverse HIV patient samples. The amplified DNA preferably comprises a portion encoding 10–900 (such as 100–400, 400–600 or 600–900, or any range or value therein) amino acids of a gp120and gp41 (both make up gp160). One or more of the envelope variable regions (V1–V5) and constant regions (C1–C5) are preferably included in the PCR products, more preferably most of the V1, C1, V2, C2, V3, C3, V4, C4, and V5regions. In addition, amplified sequences can encode 1–200 amino acids beyond the cleavage site for gp120/gp41. Preferably, most or all of the entire env gene is amplified. Optionally, the gp160 encoding sequence amplified is missing part or all of sequences encoding the transmembrane domain and/or the cytoplasmic tail domain (see, e.g.,Hallenberger et al. (1993)).

The PCR primers can be designed so that restriction enzyme sites flank the envelope gene sequence in vaccinia plasmid, such that they are incorporated into the amplified DNA products. By using well-known substitution cloning techniques, vaccinia plasmid derivatives that express envelope protein variant sequences from 1–10,000 patients can be generated by substituting a portion of the patient's EPV encoding sequence for corresponding portion of the env sequence in the vaccinia plasmid such as by using restriction fragments for the substitution. For example, the pVenv4 plasmid and PCR products are treated with KpnI and BsmI to obtain a sequence encoding a truncated gp160 of amino acids 1–639, which lacks both the transmembrane domain and the cytoplasmic tail domain of gp41 (see, e.g., Hallenberger et al.(1993)).

Following ligation of the PCR product and the pVenv products, bacterial host cells are transformed with the ligation mixture via any of a number of methods well-known in the art, including, e.g., electroporation, and recombinant colonies are picked and examined by sequencing.

Recombinant Vaccinia Virus Constructs Encoding HIV Envelope Proteins. The EPV encoding vaccinia is then recombined with wild type virus in a host cell and the EPV expressing virus plaques are selected and virus stocks made. The virus stocks as VVenv's each containing a different EPV encoding sequence are then mixed using at least 4–40, and up to about 10,000 different recombinant viruses, to form a polyenv vaccine of the present invention.

The recombinant vaccinia plasmids containing the EPV sequences are then optionally sequenced or screened with HIV envelope protein-specific antibodies to identify different EPVs. Sequencing by the Sanger Method dideoxy-chain termination is preferred. This involves the denaturation of DNA, annealing of primer, and initiation of DNA synthesis in the presence of at least one radio-labeled nucleotide, with plasmid DNA as the template. The polymerization mix is then aliquoted in different tubes and DNA synthesis is continued in the presence of one di-deoxynucleotide (ddATP, ddCTP, ddGTP, ddTTP) per tube. Each chain of newly synthesized DNA is terminated when ddNTP is incorporated. The products of each reaction are run in parallel on an acrylamide gel, which will resolve fragments differing by one nucleotide in size. Thus, the sequence can be read by identifying the ddNTP responsible for the termination of each fragment. The procedure is preferably adapted from previously described methods (Sambrook et al. (1989), infra; United States Biochemical, *Sequenase Version 2.0—DNA Sequencing Kit*, Ninth Edition, Amersham Life Science, Inc., (1994)) and should read approximately 50–300 bp from the primer position.

Methods for the production of VV expression vectors are well-known in the art (see, e.g., Mackett, M. et al., *Proc. Natl. Acad Sci.* (USA) 79:7415–7419 (1982); Panicali, D., and Paoletti, E., *Proc. Natl. Acad Sci.* (USA) 79:4927–4931 (1982); U.S. Pat. No. 4,169,763; Mazzara, G. P. et al., *Methods in Enz.* 217:557–581 (1993)). Ausubel et al., infra, at §§ 16.15–16.19, each of which are entirely incorporated herein by reference. The previously described pSC11 vector (Chakrabarti, S. et al., *Mol. Cell. Biol.* 5:3403–3409 (1985)) can preferably be used to create an env-encoded plasmid, such as pVenv4.

As a viral vector, vaccinia virus has a number of useful characteristics, including capacity that permits cloning large fragments of foreign DNA (greater than 20 Kb), retention of infectivity after insertion of foreign DNA, a wide host range, a relatively high level of protein synthesis, and suitable transport, secretion, processing and post-translational modifications as dictated by the primary structure of the expressed protein and the host cell type use. For example, N-O-glycosylation, phosphorylation, myristylation, and cleavage, as well as assembly of expressed proteins, occur in a faithful manner.

Several variations of the vaccinia vector have been developed and are suitable for use in the present invention (e.g., see Ausubel et al., infra, §§ 16.15–16.19). Most commonly, after obtaining the virus stock (Ausubel, infra at § 16.16), a nucleic acid sequence encoding an EPV is placed under control of a vaccinia virus promoter and integrated into the genome of vaccinia so as to retain infectivity (Ausubel et al., infra at § 16.17). Alternatively, expression can be achieved by transfecting a plasmid containing the vaccinia promoter-controlled gene encoding an EPV into a cell that has been infected with wild-type vaccinia.

Preferably, the host cell and vaccinia vector are suitable and approved for use in vaccination of mammals and humans. These recombinant viruses are then characterized using various known methods (Ausubel et al., infra at § 16.18). In still another variation, the bacteria phage T7 RNA polymerase chain can be integrated into the genome of vaccinia so that the EPV encoding sequences will be expressed under the control of a T7 promoter, either in transfected plasma, plasmid or a recombinant vaccinia virus, will be expressed.

The use of pox virus promoters is preferred because cellular and other viral promoters are not usually recognized by the vaccinia transcriptional apparatus. A compound early/late promoter is preferably used in recombinant vaccinia for polyenv vaccines, as it is desirable to express the EPV as an antigen that is presented in recombinant vaccinia virus infected host cell in association with major histocompatibility class (MHC) I or II. Such MHC associated HIV envelope protein will then form cytotoxic T cell targets, and prime vaccinated mammals for a cytotoxic T cell response and/or a humoral response against the expressed HIV EPVs. This is because the ability of vaccinia viral vectors to induce MHC presentation in host cells for this type of antigen appears to diminish late in the infection stage. Transcripts originating early will terminate after the sequence TTTTTNT and lead to inadequate MHC presentation.

Alternatively, any such termination motifs within the coding sequence of the gene can be altered by mutagenesis if an early pox virus promoter is used, in order to enhance MHC presentation of envelope protein antigens in host cells (Earl et al., infra, 1990). To mimic vaccinia virus mRNAs, untranslated leader and 3'-terminal sequences are usually kept short, if they are used in the vaccinia plasmids incorporating HIV EPV encoding sequences.

Preferably, the plasmid used for making vaccinia constructs according to the present invention has been designed with restriction endonuclease sites for insertion of the env gene downstream of the vaccinia promoter (Ausubel et al., infra, § 16.17). More preferably, the plasmid already contains an envelope protein encoding sequence, wherein the restriction sites occur uniquely near each of the beginning and ends of the envelope protein coding sequence. The same restriction fragment of the EPV encoding sequence can then replace the corresponding sequence in the plasmid. In such cases, the major portion of the EPV encoding sequence can be inserted after removing most or all of the envelope protein encoding sequence from the plasmid.

Preferably, the resulting vaccinia construct (containing the EPV encoding sequence and the vaccinia promoter) is flanked by vaccinia DNA to permit homologous recombination when the plasmid is transfected into cells that have been previously infected with wild-type vaccinia virus. The flanking vaccinia virus DNA is chosen so that the recombination will not interrupt an essential viral gene.

Without selection, the ratio of recombinant to parental vaccinia virus is usually about 1:1000. Although this frequency is high enough to permit the use of plaque hybridization (see Ausubel et al., infra at §§ 6.3 and 6.4) or immunoscreening (Ausubel et al., infra at § 6.7) to pick recombinant viruses, a variety of methods to facilitate recombinant-virus identification have been employed. Non-limiting examples of such selection or screening techniques are known in the art (see Ausubel et al., infra at § 16.17). Usually, the expression cassette is flanked by segments of the vaccinia thymidine kinase (TK) genes so that recombination results in inactivation of TK. Virus with a $TK^{31}$ phenotype can then be distinguished from those with a $TK^+$ phenotype by infecting a $TK^-$ cell line in the presence of 5-bromo-deoxyuridine (5-BrdU), which must be phosphorylated by TK to be lethally incorporated into the virus genome.

Alternatively or additionally, recombinant viruses can be selected by the co-expression of a bacterial antibiotic resistant gene such as ampicillin (amp) or guanine phosphoribosyl transferase (gpt). As a further example, co-expression of the *Escherichia coli lac* Z gene allows coscreening of recombinant virus plaques with Xgal (Ausubel, infra, § 16.17).

The recombinant vaccinia viruses expressing an EPV of the present invention can be optionally attenuated or inactivated according to known methods, such as by heat, paraformaldehyde treatment, ultraviolet irradiation, propriolactene treatment, hybrid or chimera formation or by other known methods (see, e.g., Zagury et al., *Nature* 332:728–731 (1988); Ito et al., *Cancer Res.* 50:6915–6918 (1990); Wellis et al., *J. Immunol.* 99:1134–9 (1967); D'Honcht, *Vaccine* 10 *Suppl.* :548–52 (1992); Selenka et al., *Arch. Hyg. Bakteriol.* 153:244–253 (1969); Grundwald-Bearch et al., *J. Cancer Res. Clin. Oncol.* 117:561–567 (1991); the contents of which are entirely incorporated here by reference. For example, heat inactivation at 60° C. will reduce virus titer considerably. Such attenuation techniques are safety tested, as incomplete inactivation might result in patient death (Dorozynski and Anderson, *Science* 252:501–502 (1991)).

Such attenuated or inactivated recombinant vaccinia is to be used where the patient may have a compromised immune system as complications or death can occur when live vaccinia is administered.

Pharmaceutical Compositions

Pharmaceutical preparations of the present invention, suitable for inoculation or for parenteral or oral administration, include a polyenv vaccine comprising of at least 4–40, and up to about 10,000, different recombinant vaccinia viruses, in the form of a cell lysate, membrane-bound fraction, partially purified or purified form. Preferably, the polyenv vaccine comprises recombinant vaccinia virus containing cell lysate (or membrane-bound fractions thereof) that further comprise EPV proteins already expressed by the recombinant vaccinia viruses. The inclusion of the expressed EPVs is now discovered to enhance the primary antibody response.

The polyenv vaccine composition can be in the form of sterile aqueous or non-aqueous solutions, suspensions, or emulsions, and can also contain auxiliary agents or excipients which are known in the art. Each of the at least about 4–40 to 10,000 different vaccinia viruses encode and express a different EPV, as presented herein. EPVs encoding DNA can be selected to represent EPVs existing in a specific isolated community of AIDS patients. For example, a vaccine could represent sequences from Memphis, Tenn. and be targeted for use in Memphis, Tenn. Vaccines designed to represent geographically restricted areas can also be useful for use in communities outside of the targeted community.

Alternatively, EPVs encoding DNAs can be selected to represent geographically distant communities, cities or countries, such as clades. For example, multiple clones can be represented in one polyenv vaccine. A polyenv vaccine composition can further comprise immunomodulators such as cytokines which accentuate an immune response to a vital infection.

See, e.g., Berkow et al., eds., *The Merck Manual*, Fifteenth Edition, Merck and Co., Rahway, N.J. (1987); Goodman et al., eds., *Goodman and Gilman's The Pharmacological Basis of Therapeutics*, Eighth Edition, Pergamon Press, Inc., Elmsford, N.Y. (1990); *Avery's Drug Treatment: Principles and Practice of Clinical Pharmacology and Therapeutics*, Third Edition, ADIS Press, LTD., Williams and Wilkins, Baltimore, Md. (1987); and Katzung, ed. *Basic and Clinical Pharmacology*, Fifth Edition, Appleton and Lange, Norwalk, Conn. (1992), which references and references cited therein, are entirely incorporated herein by reference as they show the state of the art.

As would be understood by one of ordinary skill in the art, when a polyenv vaccine of the present invention is provided to an individual, it can be in a composition which can further comprise at least one of salts, buffers, adjuvants, or other substances which are desirable for improving the efficacy of the composition. Adjuvants are substances that can be used to specifically augment at least one immune response. Normally, the adjuvant and the composition are mixed prior to presentation to the immune system, or presented separately, but into the same site of the being immunized. Adjuvants can be loosely divided into several groups based upon their composition. These groups include oil adjuvants, mineral salts (for example, $AlK(SO_4)_2$, $AlNa(SO_4)_2$, $AlNH_4(SO_4)$, silica, kaolin, and carbon), polynucleotides (for example, poly IC and poly AU nucleic acids), and certain natural substances (for example, wax D from *Mycobacterium tuberculosis*, substances found in *Corynebacterium parvum*, or *Bordetella pertussis*, and members of the genus Brucella). Among those substances particularly useful as adjuvants are the saponins (e.g., Quil A., Superfos A/S, Denmark). Examples of materials suitable for use in vaccine compositions are disclosed, e.g., in Osol, A., ed., *Remington's Pharmaceutical Sciences*, Mack Publishing Co., Easton, Pa. (1980), pp. 1324–1341, which reference is entirely incorporated herein by reference).

A pharmaceutical polyenv vaccine composition of the present invention can further or additionally comprise at least one antiviral chemotherapeutic compound. Non-limiting examples can be selected from at least one of the group consisting of gamma globulin, amantadine, guanidine, hydroxy benzimidazole, interferon-α, interferon-β, interferon-γ, interleukin-16 (IL-16; Kurth, *Nature*, Dec. 8, 1995); thiosemicarbarzones, methisazone, rifampin, ribvirin, a pyrimidine analog (e.g., AZT and/or 3TC), a purine analog, foscarnet, phosphonoacetic acid, acyclovir, dideoxynucleosides, a protease inhibitor (e.g., saquinavir (Hoffmann-La Roche); indinavir (Merck); ritonavir (Abbott Labs); AG 1343 (Agovron Pharmaceuticals); VX-2/78 (Glaxo Wellcome)); chemokines, such as RANTES, MIP1α or MIP1β (*Science* 270:1560–1561 (1995)) or ganciclovir. See, e.g., Richman: *AIDs Res. Hum. Retroviruses* 8:1065–1071(1992); *Annu Rev Pharmacol Toxico* 33:149–164 (1993); *Antimicrob Agents Chemother* 37:1207–1213 (1993); *AIDs Res. Hum. Retroviruses* 10:901 (1994); Katzung (1992), infra, and the references cited therein on pages 798–800 and 680–681, respectively, which references are herein entirely incorporated by reference.

Pharmaceutical Uses

The administration of a polyenv vaccine (or the antisera which it elicits) can be for either a "prophylactic" or "therapeutic" purpose, and preferably for prophylactic purposes. When provided prophylactically, the live polyenv vaccine composition is provided in advance of any detection or symptom of HIV infection or AIDS disease. The prophylactic administration of the compound(s) serves to prevent or attenuate any subsequent HIV infection.

When provided therapeutically, the polyenv vaccine is provided upon the detection of a symptom of actual infection. The administration of a live polyenv vaccine after HIV infection is provided only where the patient's immune system is determined to be capable of responding to administration of the live polyenv vaccine without substantive risk of unsuitable complications or death, where the administration of a live vaccinia virus is provided in the required dosage that serves to attenuate any actual HIV infection.

Alternatively, where the patients immune response is compromised, therapeutic administration preferentially involves the use of an attenuated or inactivated polyenv vaccine composition where the recombinant vaccinia viruses are attenuated or inactivated, as presented above. See, e.g., Berkow (1987), infra, Goodman (1990), infra, Avery (1987), infra and Katzung (1992), infra, Dorozynski and Anderson, *Science* 252:501–502 (1991) which are entirely incorporated herein by reference, including all references cited therein.

A composition is said to be "pharmacologically acceptable" if its administration can be tolerated by a recipient patient. Such an agent is said to be administered in a "therapeutically or prophylactically effective amount" if the amount administered is physiologically significant. A vaccine or composition of the present invention is physiologically significant if its presence results in a detectable change in the physiology of a recipient patient, preferably by enhancing a humoral or cellular immune response to an HIV.

The "protection" provided need not be absolute, i.e., the HIV infection or AIDS disease need not be totally prevented or eradicated, provided that there is a statistically significant improvement relative to a control population. Protection can be limited to mitigating the severity or rapidity of onset of symptoms of the disease.

Pharmaceutical Administration

A vaccine of the present invention can confer resistance to one or more strains of an HIV. The present invention thus concerns and provides a means for preventing or attenuating infection by at least one HIV strain. As used herein, a vaccine is said to prevent or attenuate a disease if its administration to an individual results either in the total or partial attenuation (i.e. suppression) of a symptom or condition of the disease, or in the total or partial immunity of the individual to the disease.

At least one polyenv vaccine of the present invention can be administered by any means that achieve the intended purpose, using a pharmaceutical composition as described herein.

For example, administration of such a composition can be by various parenteral routes such as subcutaneous, intravenous, intradermal, intramuscular, intraperitoneal, intranasal, transdermal, or buccal routes. Subcutaneous administration is preferred. Parenteral administration can be by bolus injection or by gradual perfusion over time. See, e.g., Berkow (1987), infra, Goodman (1990), infra, Avery (1987), infra, and Katzung (1992), infra, which are entirely incorporated herein by reference, including all references cited therein.

A typical regimen for preventing, suppressing, or treating a disease or condition which can be alleviated by a cellular immune response by active specific cellular immunotherapy, comprises administration of an effective amount of a vaccine composition as described above, administered as a single treatment, or repeated as enhancing or booster dosages, over a period up to and including one week to about 24 months.

According to the present invention, an "effective amount" of a vaccine composition is one which is sufficient to achieve a desired biological effect, in this case at least one of cellular or humoral immune response to HIV. It is understood that the effective dosage will be dependent upon the age, sex, health, and weight of the recipient, kind of concurrent treatment, if any, frequency of treatment, and the nature of the effect desired. The ranges of effective doses provided below are not intended to limit the invention and represent preferred dose ranges. However, the most preferred dosage will be tailored to the individual subject, as is understood and determinable by one of skill in the art, without undue experimentation. See, e.g., Berkow (1987), infra, Goodman (1990), infra, Avery (1987), infra, Ebadi, *Pharmacology*, Little, Brown and Co., Boston, Mass. (1985), and Katsung (1992), infra, which references and references cited therein, are entirely incorporated herein by reference.

Generally speaking, the dosage for a human adult will be from about $10^5$–$10^9$ plaque forming units (pfu)/kg or colony forming units (CFU)/kg per dose, with $10^6$–$10^8$ preferred. Whatever dosage is used, it should be a safe and effective amount as determined by known methods, as also described herein.

Subjects

The recipients of the vaccines of the present invention can be any mammal which can acquire specific immunity via a cellular or humoral immune response to HIV, where the cellular response is mediated by an MHC class I or class II protein. Among mammals, the preferred recipients are mammals of the Orders Primata (including humans, chimpanzees, apes and monkeys). The most preferred recipients are humans. The subjects preferably are infected with HIV or provide a model of HIV infection (e.g., Hu et al., *Nature* 328:721–723 (1987)), which reference is entirely incorporated herein by reference.

Having now generally described the invention, the same will be more readily understood through reference to the following example which is provided by way of illustration, and is not intended to be limiting of the present invention.

EXAMPLES

Example 1

Preparation of Vaccinia Virus Vectors for HIV Env Protein Expression

Nomenclature

For purposes of reference, a recombinant vaccinia virus construct is alternatively referred to herein as a VVenv construct, with specific vaccinia virus constructs being designated according to a patient, or to a depository (e.g., ATCC or the GenBank source of the env DNA in the construct). For example, VVenv-Doe would refer to a vaccinia virus vector construct having env sequences from patient Doe, and VVenv-U28305 would refer to a vaccinia virus vector having the env sequences found in GenBank accession No. U28305.

The polyenv vaccine consists of 4–100 distinct recombinant vaccinia viruses, each of which expresses a unique HIV-1 envelope protein. For purposes of reference, each individual virus is designated as VVenv, and the final virus mixture is referred to as polyenv.

The preparation of each VVenv uses the plasmid designated pVenv4 and a wildtype vaccinia virus designated NYCDH, described below. For additional details, see Ryan et al., "Preparation and Use of Vaccinia Virus Vectors for HIV Protein Expression and Immunization," in *Immunology Methods Manual*, Lefkovits, ed., Academic Press (1996).

Vectors and Host Cells

The previously described pSC11 vector (Chakrabarti, S. et al., *Mol. Cell. Biol.* 5:3403–3409 (1985)) can be used for the recombination of multiple HIV genes into the VV genome. Elements of the pSC11 plasmid include the lacZ gene (a reporter gene by which transformed bacteria and VV recombinants can be easily identified as those having β-galactosidase activity), a portion of the gene encoding thymidine kinase (TK), and an ampicillin resistance gene (amp). Genes cloned into pSC11 are inserted into the VV genome by homologous recombination between the TK gene of the wildtype virus and the portions of the TK gene contained in pSC11. Insertion of plasmid DNA into the viral TK locus inactivates the viral gene so that recombinant viruses can be readily selected from the background of TK$^{+}$ virus by growth in bromodeoxyuridine (BUdR). In order for recombinant TK$^{31}$ virus to survive this selection, they must be grown in cells which do not supply an active TK enzyme, such as the TK$^{-}$143 cell line, which is a TK-deficient derivative of the human cell line R970-5, an osteosarcoma cell line (Rhim, J.S. et al., *Int. J. Cancer* 15:23–29 (1975)) that supports the growth of VV (Weir et al., infra (1982)). The production of HIV gene segment expression can be by full gene insertion into the Sinai site of the pSC11 vector. Full length genes can be expressed under the control of the P7.5K promoter.

As an alternative to the cloning of complete HIV genes, one can substitute partial gene sequences for HIV genes that have already been cloned into pSC11. For example, a construct termed pVenv1 was prepared from pSC11 and expresses the BH10 HIV envelope protein (env) gene (Hallenberger et al., infra, (1993); Kilpatrick et al. *J. Biol. Chem.* 262:116–121 (1987)). The construct can be used as a parent vector to substitute and express variable envelope protein regions from field HIV isolates. Similarly, a vector termed pVenv4 was constructed from pSC11 to express a BH10 env protein, truncated to exclude the transmembrane and cytoplasmic tail domain encoding gp41 sequences while retaining the oligomerization domain (Hallenberger et al. (1993), infra). The pVenv4 vector encodes a truncated gp160 (also: gp1601, gp140) that was discovered to form a tertiary structure that is similar to that of the processed gp41/gp120 oligomer (dimer, trimer or tetramer) as is present at the cell surface of HIV infected cells. This tertiary structure is maintained in both secreted and membrane associated form (Hallenberger et al., (1993)). This vector is preferably used as a parent vector for the substitution of alternative isolated env sequences.

In this Example, the preparation of each VVenv construct involves the use of a pVenv4 and a wildtype vaccinia virus NYCDH, and appropriate host cells, as is described in detail below.

pVenv4: The pVenv4 vector was previously prepared by the insertion of an HIV-1-envelope coding sequence into the pSC11 vaccinia virus recombination vector (Hallenberger, et al., *Virology* 193:510–514 (1993); Chakrabarti et al., *Mol. Cell Biology* 5:3403–3409 (1985)). The HIV-1 sequence was derived from a laboratory stock of live virus. The sequence was named "BH10" (Ratner et al., *Nature* 313:277–284 (1985)). With PCR techniques unique envelope sequences from HIV-1 infected patients may be amplified and substituted into the BH10 env sequence to create new vectors. For example, the following primers might be used for PCR.

(A) Sense, Position 5785 (SEQ ID NO:1):

AGCAGAAGACAGTGGCAATGAGAGTGA.

(B) Antisense, Position 7694 (SEQ ID NO:2):

CCACTCCATCCAGGTCATGTTATTCCAAAT.

(C) KpnI-Sense, position 5903 (SEQ ID NO:3):

GTGGGTCACAGTCTATTATGGGGTACCTGTGT.

(D) BsmI-Antisense, position 7659 (SEQ ID NO:4):

CCAGAGATTTATTACTCCAACTAGCATTCCAAGG.

(E) (optional) DraIII-Sense, position 6153 (SEQ ID NO:5):

CCATGTGTAAAATTAACCCCACTCTGTG.

(F) (optional) Bsu36I-Anti-sense, position 6917 (SEQ ID NO:6):

TACAATTTCTGGGTCCCCTCCTGAGG.

These primers are written 5' to 3'. Restriction sites are underlined (numbered positions are based on the BH10 sequence (Ratner et al., *Nature* 313:277–284 (1985)).

PCR Strategy: In order to produce new HIV-1 env constructs, the polymerase chain reaction (PCR) is used to amplify 1800 base pairs (bp) of envelope gene from forty different HIV-1 patient samples. The PCR primers represent well-conserved HIV-1 sequences and thus successfully amplified env genes from many diverse HIV-1 patient samples. The amplified DNA encompasses the entire gp120 protein except for approximately 10 highly conserved amino acids at the protein's amino terminus. All envelope variable regions (V1–V5) are included in the PCR products. In addition, amplified sequences encode approximately 100 amino acids beyond the cleavage site for gp120/gp41.

The PCR primers carrying the restriction enzyme sites for KpnI and BsmI, which flank the BH10 envelope gene sequence in pVenv4, are incorporated into the amplified DNA products.

First Round PCR: In a 500 μl microcentrifuge tube, mix:

1 μl Primer A (SEQ ID NO:1), 300 ng/μl;

1 μl primer B (SEQ ID NO:2), 300 ng/μl;

2.5 μl 10 mM of each of 4 dNTPs;

1 μg DNA;

10 μl 10X PCR buffer; and

HPLC H20 to 99 μl

Vortex taq stock and dispense 1 μl to PCR reaction. Mix well. Overlay with mineral oil.

Run on a thermal-cycler as follows:

Incubate 95° C., 3 minutes to melt DNA.

Run 40 cycles: 95° C., 1 minute; 45° C., 2 minutes; 72° C., 3.5 minutes.

Second Round PCR: Prepare PCR reaction as above, but with primers C and D (SEQ ID NOS:3 and 4, respectively) and without the DNA. Bring the final solution to 95 μl. Overlay with mineral oil. With a plugged tip, remove 5 μl from the first PCR reaction (from below the oil). Mix the sample into the second reaction, below oil layer and begin cycles as before. Thirty cycles is usually appropriate. It can be desirable to monitor the product by removing 2 μl for gel analysis after each 10 cycles until a clear band is identified of approximately 1800 bp. By using well-known substitution cloning techniques, pVenv4, derivatives that express an env sequence from one of the 40 patients, instead of the BH10 envelope sequence, were generated. Briefly, the pVenv4 plasmid and PCR products are next cut with KpnI and BsmI, and the cut pVenv4 was run on an agarose gel and the large fragment isolated. The small fragment (1800 bp fragment) of BH10 env was discarded. The cut PCR product was also isolated and ligated to the large pVenv4 fragment to create a chimetic envelope sequence, now containing 1800 bp of the variant env from the patient DNA. Following ligation of the PCR product and the pVenv products, bacterial host cells are transformed with the ligation mixture via any of a number of methods well-known in the art, including, e.g., electroporation, and recombinant colonies are picked and examined by sequencing.

Plasmid pVenv4 or recombinants made with pVenv4 facilitates the insertion of genes into the vaccinia virus genome by homologous recombination between the tymidine kinase (Tk) gene of the wildtype virus and the Tk sequences within the plasmid. Insertion of pVenv4 DNA into the viral Tk locus yields a vaccinia virus with the HIV-1 envelope gene expressed under the control of the P7.5K early/late promoter. The virus is attenuated in growth activity due to the disruption of the Tk locus. An additional element of pVenv4 is the lacZ gene that encodes β-galactosidase activity. lacZ activity can be used to select vaccinia virus recombinants (see below).

The envelope gene expressed by pVenv4 is truncated to exclude the transmembrane/C-terminal gp41 sequence. The vector is expressed as an oligomeric structure that is found within cells and in secreted form.

Vaccinia virus-NYCDH: Each new, substituted plasmid is individually recombined with wildtype vaccinia virus NYCDH. This virus was obtained from A.T.C.C. (Accession No. VR-325) and was plaque-purified prior to use (Buck, C., and Paulino, M. S., eds., *American Type Culture Collection Catalogue of Animal Viruses and Antisera, Chlamydiae and Rickettsiae*, 6th Ed., American Type Culture Collection, Rockville, Md. (1990), p. 138).

Bacterial host cells: The plasmid may be grown on any suitable host, as known in the art (see, e.g., Ausubel, infra (1995 rev), §§ 16.15–16.19). A non-limiting example is DH5α cells.

TK-deficient cells: The transformation and vaccinia virus substitution is done on the human $Tk^-$143B cell line, which is a TK-deficient derivative of the human cell line R970-5, an osteosarcoma cell line (Rhim et al. (1975), infra) that supports the growth of VV (Weir et al. (1982), infra). Each vaccinia virus recombinant containing a unique HIV env gene sequence is selected based on expression of the lacZ gene (Virus plaques are overlayed with Bluo-gal and selected for β-galactosidase activity as judged by the development of a blue color).

Two rounds of PCR can be performed.

Example 2

Preparation of Polyenv Vaccine

Vero Cells: The final manufacturing step is to grow n VVenv constructs on Vero cells newly purchased from the A.T.C.C. (Accession No. CCL81 or X38) and cloned and expanded for virus growth. The Vero cell line has been approved by the World Health Organization for vaccine development (Hay, R., et al., eds., *American Type Culture Collection Catalogue of Cell Lines and Hybridomas*, 7th Ed., American Type Culture Collection, Rockville, Md. (1992), page 48).

Vero cells are grown with Dulbecco's Modified Eagles Medium (Bio-Whittaker), a glutamine supplement (Bio-Whittaker) and heat-inactivated fetal calf serum (Hyclone, Inc.). Alternatively, serum-free media can be used. Each VVenv construct is inoculated onto a separate confluent layer of Vero cells and harvested when cells demonstrate cytopathic effects due to virus infection. Cell extracts are washed extensively with PBS (Bio-Whittaker) after harvest and before freezing. The cells are then broken open by freeze-thawing, sonication or centrifuging at low speed in a centrifuge (optional). Aliquots of supernatant are then stored at −70° C. Envelope protein is present in the lysate at sufficient concentrations to elicit HIV envelope protein-specific antibody (as detectable by ELISA) in mammal models, even if VV is attenuated, e.g., prep is heated to 60° C., 1 hr.

The Vaccine Product: Each virus (VVenv construct) stock from Vero cells is individually frozen and subsequently titered and safety tested. After tests have been completed, aliquots of each virus are mixed to yield a stock vaccine of $10^8$ total pfu/ml ("pfu" stands for plaque-forming units). If 40 VVenv constructs are utilized, each VVenv is preferably equally represented, each VVenv used at a titer of $2.5\times10^6$ pfu/ml in the vaccine product. This should yield $1\times10^8$ total pfu.

Evaluation of Polyenv Vaccine

Mice: Mice can be infected with an intraperitoneal injection of $1\times10^7$ pfu env-expressing VV. Antibody can be identified by HIV ELISA or neutralization assays, as described above, three weeks after VV injections.

Prior to manufacture of the polyenv vaccine for human use, a similar group of viruses has been prepared for the purpose of vaccine testing in mice. These viruses were administered to mice either by the intraperitoneal or subcutaneous route. We then tested serum HIV-1-specific antibody serum was tested for activity in an enzyme-linked immunosorbant assay (ELISA). The assay involved the plating of whole, disrupted HIV-1 ($HTLV_{IIIB}$) on ELISA plates and the blocking of plates with bovine serum albumin. Serum samples were then added at dilutions of 1:100, 1:1,000 and 1:10,000 in phosphate-buffered saline. The assay was developed with an alkaline-phosphatase-conjugated goat-anti-mouse immunoglobulin antibody and p-nitrophenyl phosphate. The color reaction was stopped with a sodium hydroxide solution, and the optical density reading was taken on an ELISA plate reader at 405 nm.

Figure 2:
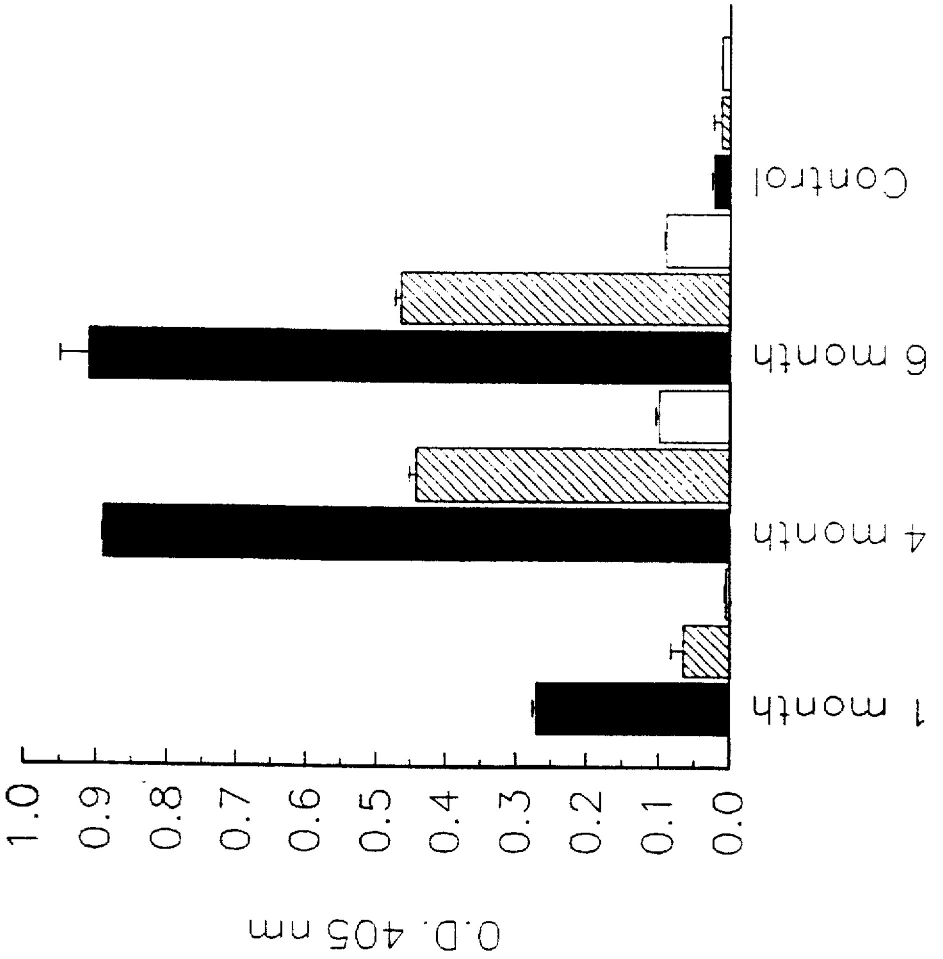
FIG. 2 is a graphical representation of data showing that the HIV-specific antibody response is long term in mammal models. The results of representative mouse sera tested in the ELISA for HIV-specific antibodies are shown. Each sample was diluted 1:100 (solid bars), 1:1,000 (hatched bars) and 1:10,000 (clear bars) prior to assay on HIV-1-coated ELISA plates. Test mice were sampled at various times (1 month, 4 months and 6 months) following the injection of $10^7$ pfu of a vaccinia virus construct expressing one envelope protein of HIV-1. The control mouse was immunized with a vaccinia virus containing no envelope sequence. Standard error bars are shown.
Figure 3:
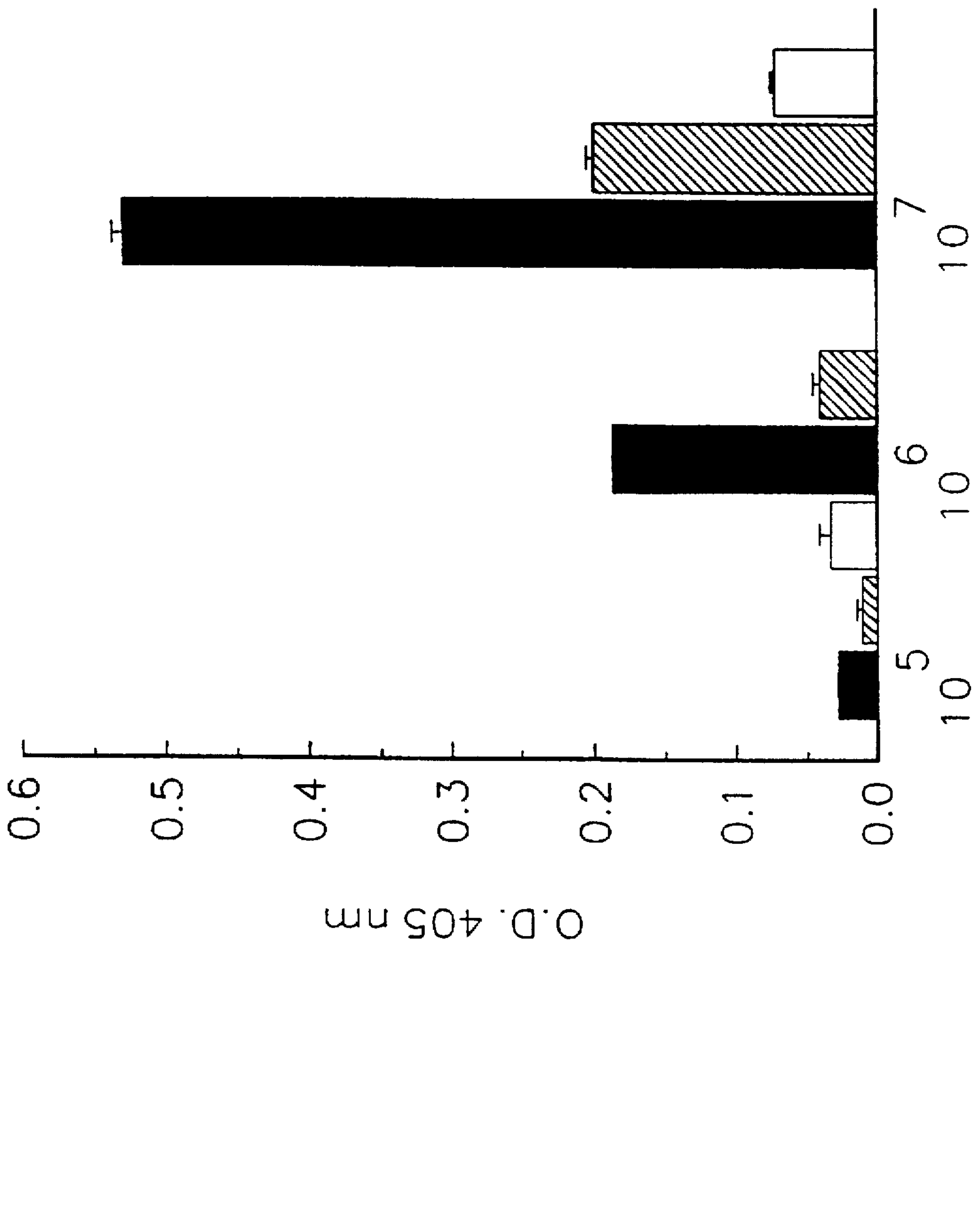
FIG. 3 is a graphical representation of data showing how the vaccinia virus dose affects the induction of at least one immune response, including HIV-specific antibody production. Representative mouse serum samples were tested by the ELISA on HIV-1-coated plates. Serum samples were taken from mice injected with $10^5$, $10^6$, and $10^7$ pfu of one vaccinia virus expressing the HIV-1-envelope protein. Serum samples were tested approximately three weeks after injection. Each sample was diluted 1:100 (solid bars), 1:1,000 (hatched bars) and 1:10,000 (clear bars) prior to assay on HIV-1-coated ELISA plates. Standard error bars are shown.

As shown in FIG. 2, a single inoculation with cell lysate preparation of $10^6$–$10^7$ pfu vaccinia virus (containing a single HIV-1/envelope protein encoding sequence and membrane bound expressed envelope protein) elicited a strong antibody response toward HIV-1 that was sustained throughout the experimental time course of six months. Such an antibody response was significantly higher than previously reported with other immunizations. This high antibody response may be attributed to the presence of membrane bound envelope protein in a vaccine preparation. As shown in FIG. 3, these responses were dose dependent. Lower responses were seen in mammals given a dose of $10^6$ pfu than in mammals given a dose of $10^7$ pfu.

Figure 4:
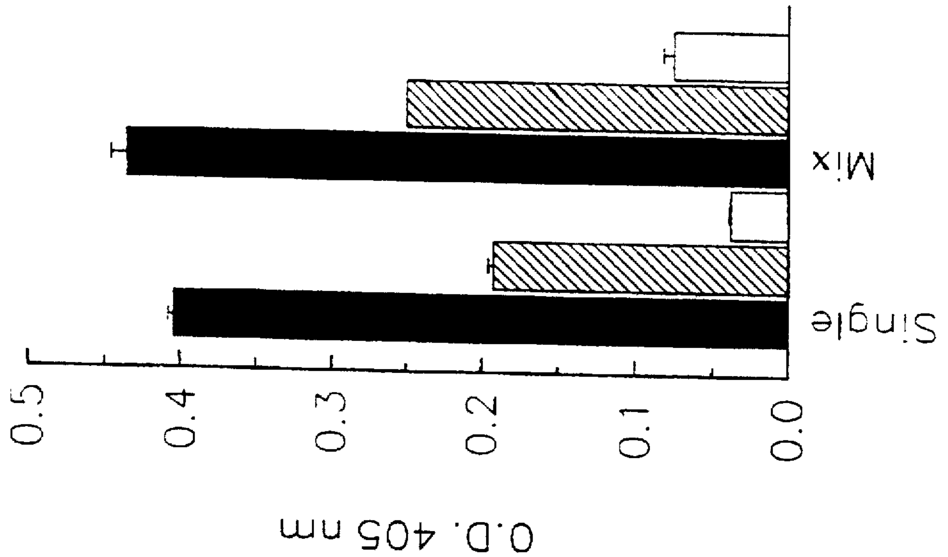
FIG. 4 is a graphical representation of data showing that the mixing of vaccinia virus constructs does not compromise the elicitation of HIV-specific antibody in injected mammals. Representative mouse serum samples were tested by the ELISA approximately 2 months following the injection of $10^7$ pfu vaccinia virus expressing HIV-1 envelope protein(s). "Single" identifies a sample from a mouse that received a single vaccinia virus. "Mix" represents a sample from a mouse that received a mixture of vaccinia viruses expressing five distinct envelope proteins. Each sample was diluted 1:100 (solid bars), 1:1,000 (hatched bars) and 1:10,000 (clear bars) prior to assay on HIV-1-coated ELISA plates. Standard error bars are shown.

Mixtures of vaccinia viruses expressing different HIV-1 envelope proteins were also prepared. When mice received $10^7$ pfu of a mixture of five viruses, their responses were essentially identical in magnitude to responses generated against $10^7$ pfu of a single vaccinia virus recombinant (FIG. 4). The mixing of numerous env-expressing vaccinia viruses in high numbers has not been reported, and is expected to provide broad spectrum of neutralizing antibody.

Chimpanzees: The mixed vaccine is expected to neutralize a higher number of challenge viruses. Two chimpanzees are injected, each with a mixture of 10–40 VVenv, with approximately $3\times10^7$ total pfu/mammal by the subcutaneous route. Two additional chimpanzees receive $3\times10^7$ total pfu/mammal of a single VVenv. It is expected that the mammals will generate antibody responses capable of neutralizing HIV-1 isolates in laboratory tests, and that the neutralization will be superior with immune sera from the mammals injected with 10–40 VVenv, as a polyenv vaccine of the present invention, as compared to sera from mammals immunized with 1–3 vaccinia viruses expressing: (1) one or several variable regions of the HIV envelope protein, such as the V3 region; (2) one HIV envelope proteins; or (3) one or several portions of the variable and constant regions from 1–3 HIV envelope proteins.

Humans: Tests of the mixed virus stock are performed prior to clinical trials, the first of which will be for the purpose of dose escalation and safety testing.

The clinical trials will be a dose escalation study involving the assembly of four volunteer groups. Each group receives one of the following vaccine doses:

(1) $2\times10^4$ pfu (2) $2\times10^5$ pfu (3) $2\times10^6$ pfu (4) $2\times10^7$ pfu Each volunteer receives the mixed virus vaccine in 0.5 ml saline, administered by a subcutaneous injection.

REFERENCE LIST

Ausubel et al., eds, *Current Protocols in Molecular Biology*, Greene Publishing Assoc., New York, N.Y. (1987, 1988, 1989, 1990, 1991, 1992, 1993, 1994, 1995)

*Avery's Drug Treatment: Principles and Practice of Clinical Pharmacology and Therapeutics*, Third Edition, ADIS Press, LTD., Williams and Wilkins, Baltimore, Md. (1987)

Belshe, R. B. et al., *J. Am. Med. Assoc.* 272:431–431 (1994)

Berkow et al., eds., *The Merck Manual*, Fifteenth Edition, Merck and Co., Rahway, N.J. (1987)

Birnboim, H. C. and Doly, J., *Nucleic Acids Res.* 7:1513–1523 (1979)

Buck, C., and Paulino, M. S., eds., *American Type Culture Collection Catalogue of Animal Viruses and Antisera, Chlamydiae and Rickettsiae*, 6th Ed., American Type Culture Collection, Rockville, Md. (1990)

Burns, D. P. W. and Desrosiers, R. C., *Cur. Topics Microbial. Immunol.* 188:185–219 (1994)

Chakrabarti, S. et al., *Mol. Cell. Biol.* 5:3403–3409 (1985)

Cooney et al., *Proc. Natl. Acad. Sci.* USA 90:1882–1886 (1993)

Creighton, T. E., *Proteins: Structure and Molecular Properties*, W. H. Freeman & Co., San Francisco, Calif. (1983)

DeVita Jr., V. T. et al., *AIDS, Etiology, Diagnosis, Treatment and Prevention*, 3rd edition, J. B. Lippincott Co., Philadelphia, Pa. (1992)

D'Honcht, *Vaccine* 10 *Suppl.* :548–52 (1992)

Dorozynski and Anderson, *Science* 252:501–502 (1991)

Ebadi, *Pharmacology*, Little, Brown and Co., Boston, Mass. (1985)

Eichberg, *Int. Conf. AIDS* 7:88 (1991)

Embretson, J. et al., *Nature* 362:359–362 (1993)

Enami et al., *J. Virol.* 65:2711–2713 (1991)

Enami et al., *Proc. Natl. Acad. Sci.* USA 87:3802–3805 (1990)

Fauci, *Science* 264:1072–1073 (1994)

Goodman et al., eds., *Goodman and Gilman's The Pharmacological Basis of Therapeutics*, Eighth Edition, Pergamon Press, Inc., Elmsford, N.Y. (1990)

Gorse, *AIDS Res. Hum. Retrovir.* 10 (Suppl. 2):141–143 (1994)

Gribskov and Burgess, *Nucl. Acids Res.* 14:6745 (1986)

Graham et al., *J. Infect. Dis.* 166:244–252 (1992); *J. Infect. Dis.* 167:533–537 (1993)

Grundwald-Bearch et al., *J Cancer Res. Clin. Oncol.* 117:561–567 (1991)

Hallenberger et al., *Virology* 193:510–514 (1993)

Hay, R., et al., eds., *American Type Culture Collection Catalogue of Cell Lines and Hybridomas*, 7th Ed., American Type Culture Collection, Rockville, Md. (1992)

Hirsch, M. S., and Curran, J. *"Human immunodeficiency viruses, biology and medical aspects,"* in *Virology*, Fields and Knipe, eds., Raven Press, Ltd., New York, N.Y. (1990), pp 1545–1570

Hu et al., *Nature* 328:721–723 (1987)

Ish-Horowicz, D. and Burke, J. F., *Nucleic Acids Res.* 9:2989–2998 (1981)

Ito et al., *J. Virol.* 65:5491–5498 (1991)

Ito et al., *Cancer Res.* 50:6915–6918 (1990)

Javaherian, K. et al., *Proc. Natl. Acad Sci.* (USA) 86:6768–6772 (1989)

Katzung, ed., *Basic and Clinical Pharmacology*, Fifth Edition, Appleton and Lange, Norwalk, Conn. (1992)

Keefer et al., *AIDS Res. Hum. Retrovir.* 10 (Suppl. 2):S139–143 (1994)

Kieny et al., *Int. Conf. AIDS* 5:541 (1989)

Kilpatrick et al. *J. Biol. Chem.* 262:116–121 (1987)

Luytjes et al., *Cell* 59:1107–1113 (1989)

Mackett, M. et al., *Proc. Natl. Acad. Sci.* (USA) 79:7415–7419 (1982)

Mazzara, G. P. et al., *Methods in Enz.* 217:557–581 (1993)

McElrath et al., *J. Infect. Dis.* 169:41–47 (1994)

Needleman and Wunsch, *J. Mol. Biol.* 48:443 (1970)

Osol, A., ed., *Remington's Pharmaceutical Sciences*, Mack Publishing Co., Easton, Pa. (1980), pp. 1324–1341

Panicali, D., and Paoletti, E., *Proc. Natl. Acad Sci.* (USA) 79:4927–4931 (1982)

Pantaleo, G. et al., *Nature* 362:355–358 (1993)

Rhim, J. S. et al., Int. *J. Cancer* 15:23–29 (1975)

Richman, *AIDs Res. Hum. Retroviruses* 8:1065–1071 (1992);

Richman, *Annu Rev Pharmacol Toxico* 33:149–164 (1993);

Richman, *Antimicrob Agents Chemother* 37:1207–1213 (1993);

Richman, *AIDs Res. Hum. Retroviruses* 10:901 (1994)

Richmond and McKinney, eds, *Biosafety in microbiological and biomedical laboratories*, 3rd Edition, U.S. Dept. of Health & Human Services, Washington D.C. (1993)

Sambrook, J. et al., *Molecular Cloning: A Laboratory Manual*, Second Edition, Cold Spring Harbor Laboratory Press, Cold Spring Harbor, N.Y. (1989)

Schulz, G. E. et al., *Principles of Protein Structure*, Springer-Verlag, New York, N.Y. (1978)

Schwartz and Dayhoff, eds., *Atlas of Protein Sequence and Structure*, National Biomedical Research Foundation, |Washington, D.C. ?–wp| (1979), pp. 353–358

Selenka et al., *Arch. Hyg. Bakteriol.* 153:244–253 (1969)

Smith and Waterman, *Adv. Appl. Math.* 2:482 (1981)

Starcich et al., *Cell* 45:637 (1986)

Towbin, H. et al., *Proc. Natl. Acad. Sci.* (USA) 76:4350 (1979)

United States Biochemical, *Sequenase Version 2.0-DNA Sequencing Kit*, Ninth Edition, Amersham Life Science, Inc., Boise, Id. (1994)

Weir et al., *Proc. Natl. Acad. Sci.* U.S.A. 79:1210–1214 (1982)

Wellis et al. *J. Immunol.* 99:1134–9 (1967)

Wong-Staal, F., *"Human immunodeficiency viruses and their replication," in Virology*, Fields and Knipe, eds., Raven Press, Ltd., New York, N.Y. (1990), pp 1529–1543

Wrin et al., *J. Acquit. Immune Defic. Syndr.* 7:211–219 (1994)

Wu et al., *Prog. Nucl. Acid. Res. Molec. Biol.* 21:101–141 (1978)

Zagury el al., *Nature* 332:728–731 (1988)

What is claimed is:

1. An immunogenic composition that can elicit an immune response to more than one but not necessarily all of the env variants contained in the composition, comprising at least 4 to about 10,000 recombinant vaccinia viruses, each comprising an env variant (EV) nucleotide encoding a different envelope protein variant of a human immunodeficiency virus (HIV), wherein (i) said EV nucleotide encodes both variable and constant regions of said envelope protein variant; and (ii) said immunogenic composition is capable of eliciting at least one of a cellular and a humoral immmune response in a mammal against an HIV strain.

2. The immunogenic composition according to claim 1, wherein said envelope protein variant comprises gp120 and an oligomerization domain of gp41.

3. The immunogenic composition according to claim 2, wherein said EV nucleotide is isolated from a patient infected with an HIV virus.

4. The inmmunogenic composition according to claim 2, wherein said EV nucleotide comprises a KpnI-BsmI restriction fragment of an HIV envelope protein encoding nucleotide.

5. The immunogenic composition according to claim 1, wherein said immunogenic composition further comprises envelope protein variants expressed by said recombinant vaccinia viruses.

6. The immunogenic composition according to claim 1, wherein said immunogenic composition further comprises at least one of a pharmaceutically acceptable carrier, an adjuvant and an antiviral chemotherapeutic compound.

7. A method for making a immunogenic composition that can elicit an immune response to more than one but not necessarily all of the env variants contained in the composition, comprising combining in admixture at least 4 to about 10,000 recombinant viruses to obtain a immunogenic composition, wherein (i) each of said recombinant viruses comprises an env variant (EV) nucleotide encoding a different envelope protein variant of an HIV envelope protein;

(ii) said EV nucleotide encodes both variable and constant regions of said envelope protein variant; and (iii) said immunogenic composition is capable of eliciting at least one of a cellular and a humoral immune response in a mammal against an HIV strain.

8. A method according to claim 7, wherein said immunogenic composition further comprises envelope protein variants expressed by said recombinant vaccinia viruses.

9. A method according to claim 7, wherein said envelope protein variant comprises gp120 and an oligomerization domain of gp41.

10. A method according to claim 7, wherein said EV nucleotide is isolated from a patient infected with an HIV virus.

11. A method according to claim 9, wherein said EV nucleotide comprises a KpnI-BsmI restriction fragment of an HIV envelope protein encoding nucleotide.

12. A method according to claim 7, wherein said combining step further comprises adding at least one pharmaceutically acceptable carrier, adjuvant and an antiviral chemotherapeutic compound.

13. A method for eliciting a humoral or cellular immune response, or both, to a human immunodeficiency virus (HIV) in a mammal, comprising administering to said mammal an effective amount of a immunogenic composition comprising at least 4 to about 10,000 different recombinant viruses, wherein (i) each of said recombinant viruses comprises an env variant (EV) nucleotide encoding a different envelope protein variant of an HIV envelope protein;

(ii) said EV nucleotide encodes both variable and constant regions of said envelope protein variant; and (iii) said amount of said immunogenic composition is effective to elicit at least one of a cellular and a humoral immune response in said mammal against an HIV strain infecting said mammal.

14. A method according to claim 13, wherein said immunogenic composition further comprises variant envelope proteins expressed by said recombinant vaccinia viruses.

15. A method according to claim 13, wherein said said envelope protein variant comprises gp120 and an oligomerization domain of gp41.

16. A method according to claim 13, wherein said EV nucleotide is isolated from a patient infected with an HIV virus.

17. A method according to claim 15, wherein said EV nucleotide comprises a KpnI-BsmI restriction fragment of an HIV envelope protein encoding nucleotide.

18. A method according to claim 13, wherein said administering step further comprises administering at least one pharmaceutically acceptable carrier, adjuvant or an antiviral chemotherapeutic compound.

* * * * *

UNITED STATES PATENT AND TRADEMARK OFFICE

CERTIFICATE OF CORRECTION

PATENT NO. : 5,741,492
DATED : January 23, 1996
INVENTOR(S) : Hurwitz et al.

It is certified that error appears in the above-identified patent and that said Letters Patent is hereby corrected as shown below:

Column 31,
Lines 59 and 63, "nucleotide" should read -- nucleic acid --;

Column 32,
Lines 5, 8, 9-10, 27, 30, 43, 46, 47, 59 and 61, "nucleotide" should read -- nucleic acid --;
Line 15, "viruscs" should read -- viruses --;

Column 33,
Line 4, "nucleotide" should read -- nucleic acid --;
Line 8, "said said" should read -- said --;

Column 34,
Lines 2 and 3, "nucleotide" should read -- nucleic acid --.

Signed and Sealed this

Sixteenth Day of May, 2006

JON W. DUDAS
*Director of the United States Patent and Trademark Office*

UNITED STATES PATENT AND TRADEMARK OFFICE

CERTIFICATE OF CORRECTION

PATENT NO. : 5,741,492
APPLICATION NO. : 08/590288
DATED : April 21, 1998
INVENTOR(S) : Hurwitz et al.

It is certified that error appears in the above-identified patent and that said Letters Patent is hereby corrected as shown below:

Column 31,
Lines 59 and 63, "nucleotide" should read -- nucleic acid --;

Column 32,
Lines 5, 8, 9-10, 27, 30, 43, 46, 47, 59 and 61, "nucleotide" should read -- nucleic acid --;
Line 15, "viruscs" should read -- viruses --;

Column 33,
Line 4, "nucleotide" should read -- nucleic acid --;
Line 8, "said said" should read -- said --;

Column 34,
Lines 2 and 3, "nucleotide" should read -- nucleic acid --.

This certificate supersedes Certificate of Correction issued May 16, 2006.

Signed and Sealed this

Fourth Day of July, 2006

JON W. DUDAS
*Director of the United States Patent and Trademark Office*